US009962445B2

(12) United States Patent
Moro et al.

(10) Patent No.: US 9,962,445 B2
(45) Date of Patent: *May 8, 2018

(54) EMULSIONS OR MICROEMULSIONS FOR USE IN ENDOSCOPIC MUCOSAL RESECTIONING AND/OR ENDOSCOPIC SUBMUCOSAL DISSECTION

(71) Applicant: COSMO TECHNOLOGIES LTD., Dublin (IE)

(72) Inventors: Luigi Moro, Lainate (IT); Luigi Maria Longo, Lainate (IT); Enrico Frimonti, Lainate (IT); Alessandro Repici, Turin (IT)

(73) Assignee: COSMO TECHNOLOGIES LTD., Dublin (IE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/334,496

(22) Filed: Oct. 26, 2016

(65) Prior Publication Data

US 2017/0043018 A1 Feb. 16, 2017

Related U.S. Application Data

(60) Continuation of application No. 15/154,857, filed on May 13, 2016, now Pat. No. 9,522,216, which is a continuation of application No. 14/950,525, filed on Nov. 24, 2015, now Pat. No. 9,364,580, which is a division of application No. 14/546,925, filed on Nov. 18, 2014, now Pat. No. 9,226,996.

(30) Foreign Application Priority Data

Nov. 20, 2013 (IT) .............. MI2013A1924

(51) Int. Cl.
| | | |
|---|---|---|
| *A61K 47/00* | (2006.01) | |
| *A61K 47/34* | (2017.01) | |
| *A61K 49/00* | (2006.01) | |
| *A61L 24/00* | (2006.01) | |
| *A61L 24/04* | (2006.01) | |
| *A61K 9/00* | (2006.01) | |
| *A61K 9/107* | (2006.01) | |
| *A61K 47/10* | (2017.01) | |
| *A61K 47/22* | (2006.01) | |
| *A61L 31/06* | (2006.01) | |
| *A61L 31/14* | (2006.01) | |
| *A61K 47/02* | (2006.01) | |
| *A61K 47/14* | (2017.01) | |

(52) U.S. Cl.
CPC .......... *A61K 47/34* (2013.01); *A61K 9/0019* (2013.01); *A61K 9/107* (2013.01); *A61K 9/1075* (2013.01); *A61K 47/02* (2013.01); *A61K 47/10* (2013.01); *A61K 47/14* (2013.01); *A61K 47/22* (2013.01); *A61K 49/006* (2013.01); *A61L 24/001* (2013.01); *A61L 24/0005* (2013.01); *A61L 24/046* (2013.01); *A61L 31/06* (2013.01); *A61L 31/14* (2013.01); *A61L 2300/442* (2013.01); *A61L 2400/06* (2013.01)

(58) Field of Classification Search
USPC ....................................................... 514/784
See application file for complete search history.

(56) References Cited

U.S. PATENT DOCUMENTS

| | | | |
|---|---|---|---|
| 3,740,421 A | 6/1973 | Schmolka et al. | |
| 7,909,809 B2 | 3/2011 | Scopton et al. | |
| 8,282,621 B2 | 10/2012 | Scopton et al. | |
| 8,864,738 B2 | 10/2014 | Scopton et al. | |
| 9,226,996 B2 | 1/2016 | Moro et al. | |
| 9,364,580 B2* | 6/2016 | Moro ............... | A61K 9/0019 |
| 9,522,216 B2* | 12/2016 | Moro ............... | A61K 9/0019 |
| 2005/0220831 A1 | 10/2005 | Jorsal | |
| 2011/0052490 A1 | 3/2011 | Vogel | |

FOREIGN PATENT DOCUMENTS

| | | |
|---|---|---|
| EP | 2 494 957 A1 | 9/2012 |
| WO | 93/18852 A1 | 9/1993 |
| WO | 00/78301 A1 | 12/2000 |
| WO | 2009/070793 A1 | 6/2009 |
| WO | 2011/103245 A1 | 8/2011 |

OTHER PUBLICATIONS

Repici et al. "Standard Needle versus needless injection modality: animal study on different fluids for submucosal elevation" Gastrointestinal Endoscopy (Jan. 2017), doi: 10.2016/j.gie.2017.01.029—19 pages.
European Search Report dated Oct. 10, 2016, issued for European patent apln. No. 16179259.3 , 13 pages.
Polymeros, D. et al., "Comparative Performance of Novel Solutions for Submucosal Injection in Porcine Stomachs: An Ex Vivo Study," Digestive and Liver Disease, 2010, vol. 42, pp. 226-229.
Jeppsson, R. et al., "The Influence of Emulsifying Agents and of Lipid Soluble Drugs on the Fractional Removal Rate of Lipid Emulsions from the Blood Stream of the Rabbit," Acta Pharmacol. et Toxicol., 1975, vol. 37, pp. 134-144.

(Continued)

*Primary Examiner* — Rei Tsang Shiao
(74) *Attorney, Agent, or Firm* — Rothwell, Figg, Ernst & Manbeck, P.C.

(57) ABSTRACT

The present invention relates to a pharmaceutical composition in form of emulsion or microemulsion and the use thereof as aid during endoscopic procedures in which it is injected in a target tissue in order to form a cushion. More in details, the invention relates to a method for performing an endoscopic procedure, which comprises injecting said pharmaceutical composition in form of emulsion or microemulsion in a target tissue of a patient, in order to form a cushion, which cushion is then optionally subjected to an endoscopic surgical procedure, such as a resection.

20 Claims, 16 Drawing Sheets

(56) References Cited

OTHER PUBLICATIONS

Fernandez-Esparrach, G. et al., "Efficacy of a Reverse-Phase Polymer as a Submucosal Injection Solution for EMR: A Comparative Study (with video)," Gastrointestinal Endoscopy, 2009, vol. 69, No. 6, pp. 1135-1139.

Uraoka, T. et al., "Submucosal Injection Solution for Gastrointestinal Tract Endoscopic Mucosal Resection and Endoscopic Submucosal Dissection," Drug Design, Development and Therapy, 2008, vol. 2, pp. 131-138.

Eun, S.H. et al., "Effectives of Sodium Alginate as a Submucosal Injection Material for Endoscopic Mucosal Resection in Animal," Gut and Liver, vol. 1, No. 1, 2007, pp. 27-32.

Escobar-Chavez, J.J. et al., "Applications of Thermo-Reversible Pluronic F-127 Gels in Pharmaceutical Formulations," J. Pharm. Pharmaceutic Sci (www.cspsCanada.org), 2006, vol. 9, No. 3, pp. 339-358.

Yapar, E.A. et al., "Poly(ethylene oxide)-Poly(propylene oxide)-Based Copolymers for Transdermal Drug Delivery: An Overview," Tropical Journal of Pharmaceutical Research, 2012, vol. 11, No. 5, pp. 855-866.

Eccleston, G.M., "Emulsions and Microemulsions," Encyclopedia of Pharmaceutical Technology, pp. 1548-1565, copyright 2007 by Informa Healthcare USA, Inc.

Italian Search Report and Written Opinion, Applicant: Cosmo Technologies Limited, Application No. ITMI20131924, dated Jul. 24, 2014, 11 pages.

Mayo Clinic, Clinical Update, Current Trends in the Practice of Medicine, 2011, vol. 27, No. 6, 2 pages.

\* cited by examiner

EMULSIONS OR MICROEMULSIONS FOR USE IN ENDOSCOPIC MUCOSAL RESECTIONING AND/OR ENDOSCOPIC SUBMUCOSAL DISSECTION

CROSS-REFERENCE TO RELATED APPLICATIONS

The present application is a continuation of U.S. patent application Ser. No. 15/154,857 filed 13 May 2016, now U.S. Pat. No. 9,522,216, which in turn is a continuation of U.S. patent application Ser. No. 14/950,525 filed 24 Nov. 2015, now U.S. Pat. No. 9,364,580, which in turn is a division of U.S. patent application Ser. No. 14/546,925 filed 18 Nov. 2014, now U.S. Pat. No. 9,226,996, which claims priority to Italian application No. MI2013A001924 filed 20 Nov. 2013. Each application is incorporated herein by reference in its entirety.

FIELD OF THE INVENTION

The present invention relates to a pharmaceutical composition in form of emulsion or microemulsion and the use thereof as aid during endoscopic procedures in which it is injected in a target tissue in order to form a cushion. More in details, the invention relates to a method for performing an endoscopic procedure, which comprises injecting said pharmaceutical composition in form of emulsion or microemulsion in a target tissue of a patient, in order to form a cushion, which cushion is then optionally subjected to an endoscopic surgical procedure, such as a resection.

BACKGROUND OF THE INVENTION

Endoscopy is a diagnostic and medical procedure which allows to examine the interior of a hollow organ or cavity of the body by means of an instrument called endoscope, without employing invasive surgery. Endoscopy is commonly used for diagnostic purposes, even though minor, non-invasive surgical and non-surgical interventions can be performed during an endoscopic procedure. Typically, said minor interventions comprise cauterization of a bleeding vessel, widening a narrow esophagus, removing polyps, adenomas and small tumors, performing biopsies or removing a foreign object. Endoscopy is used by specialists to examine, for example, the gastrointestinal tract, the respiratory tract, the ear, the urinary tract, the female reproductive system and, through small incisions, normally closed body cavities such as the abdominal or pelvic cavity (laparoscopy), the interior of a joint (arthroscopy) and organs of the chest (thoracoscopy and mediastinoscopy). The endoscope is an illuminated usually optic fiber flexible or rigid tubular instrument for visualizing the interior of a hollow organ or part (as the bladder, esophagus, stomach or intestine) for diagnostic or therapeutic purposes, that typically has one or more working channels to enable passage of instruments (such as forceps, electrosurgical knife, endoscopic injection needles or scissors) or to facilitate the removal of bioptic samples. It includes a suitable lamp and imaging device at its distal portion, and it can be inserted through natural occurring openings of the body, such as the mouth, the anus, the ear, the nose or through small surgical incisions. Given the wide variety of body organs or cavities which can be examined by means of endoscopic procedures, several types of endoscopes exist, such as, for example, laryngoscope, thoracoscope, angioscope, colonoscope, enteroscope, sigmoidoscope, rectoscope, proctoscope, anoscope, arthroscope, rhinoscope, laparoscope, hysteroscope, encephaloscope, nephroscope, esophagoscope, bronchoscope, gastroscope, amnioscope, cystoscope.

In particular, endoscopic procedures are widely applied in the gastrointestinal tract, both for diagnostic purposes and for small interventions. With the progress advance of the imaging technology, endoscopic procedures can be used to accurately examine the mucosa that covers the gastrointestinal cavities, and to detect small and large pathological lesions, such as inflammatory tissue, polyps, pseudo-polyps, serrated lesions, adenomas, ulcerations, dysplasias, pre-neoplastic and neoplastic formations, tumors and similar. In addition, endoscopic procedures in the gastrointestinal tract allow the doctor to perform minor, surgical or non-surgical interventions, which comprise, for example, biopsies and removal of pathologic lesions (polyps, adenomas, dysplasias, Barrett's dysplasia, pre-neoplastic and neoplastic formations, tumors). Surgical interventions include two endoscopic resection procedures commonly used in gastrointestinal endoscopy to remove pathological lesions: endoscopic mucosal resection (EMR) and endoscopic submucosal dissection (ESD). These two techniques have provided new alternatives for minimally invasive treatment of gastrointestinal polyps, adenomas, dysplasias, Barrett's dysplasia and early-stage cancers that involve a minimum risk of lymph-node metastasis. EMR is an endoscopic technique developed for removal of sessile or flat neoplasms confined to the superficial layers (mucosa and submucosa) of the GI tract. EMR is typically used for removal of lesions smaller than 2 cm or piecemeal removal of larger lesions. EMR also plays an important role in the assessment of resected specimens for accurate pathological staging. In contrast to polypectomy, EMR involves the lifting up of a lesion from the muscular layer by injecting a fluid agent, commonly normal saline (NS) solution, into the submucosal layer. EMR is also useful for obtaining specimens for accurate histopathological staging to determine the risk of lymph-node metastasis. EMR facilitates the complete removal of the affected mucosa by excising through the middle or deeper portion of the gut wall submucosa. Various EMR techniques have been described and four methods involving snare resection are commonly used: (1) the inject and cut method; (2) the inject, lift, and cut method; (3) cap-assisted EMR (EMRC); and (4) EMR with ligation (EMRL). The inject and cut technique, also known as submucosal injection polypectomy, has become widely used in recent years because of its simplicity. The diseased mucosa is lifted up from the muscular layer by creating a submucosal fluid cushion, captured, strangulated using an electrosurgical snare, and then resected. However, injection into the thin submucosal layer is a delicate process, the injected solution tends to dissipate quickly, flat and depressed lesions are hard to capture with the snare compared with protruded lesions, and large or awkwardly located lesions can be difficult to remove (Uraoka et al., Drug Design, Development and Therapy 2008:2 131-138). Injection-assisted EMR is frequently used for large flat colon polyps.

Endoscopic submucosal dissection (ESD), a relatively new endoscopic resection procedure, was specifically developed for removing larger lesions. Lesions are dissected directly along the submucosal layer using an electrosurgical knife, resulting in an en-bloc resection of even large lesions. ESD has been predicted to replace conventional surgery in treating certain cancerous stages, but since it has a higher rate of perforation and bleeding complications than conventional EMR, a greater degree of endoscopic skill and experience is required than for EMR. Various submucosal injection solutions had previously been developed and shown to be satisfactory for use during EMR, but introduction of the lengthier ESD procedure required a longer-lasting solution to help identifying the cutting line during dissection of the submucosal layer (Uraoka et al., Drug Design, Development and Therapy 2008:2 131-138).

The use of submucosal injection is essential for a successful EMR, as injection of fluid into the submucosa cushions facilitates the isolation of the tissue to be removed just before capture of the target lesion with a snare, thereby reducing thermal injury and the risk of perforation and haemorrhage while also facilitating an en-bloc resection. Submucosal injection is considered to play an important role in the EMR procedure, and the "ideal" submucosal injection solution should be both long-lasting as regards cushion duration and capable of producing a hemispheric shape to facilitate snaring. In addition, providing a sufficiently high submucosal elevation is important for safe submucosal cutting during the ESD procedure (Uraoka et al., Drug Design, Development and Therapy 2008:2 131-138).

The ideal solution for injection-assisted EMR should be safe, inexpensive, non toxic, readily available, easy to inject and especially it should be capable of providing a high, long-lasting submucosal cushion. Wound healing characteristics should be also requested to facilitate the closure of the wound created by the removal of the resected mucosa, as well as the presence of a colouring agent (such as a dye) to allow an improvement in distinguishing more easily the deepness of the muscolaris mucosa, avoiding undue perforation during ESD.

Normal saline solution (NS) has been commonly used for this purpose, but it is difficult to produce the proper submucosal fluid cushion and maintain the desired height, particularly for flat elevated lesions, because of the rapid dispersion of the solution through the mucosal layers and absorption of NS into the surrounding tissue (Uraoka et al., Drug Design, Development and Therapy 2008:2 131-138). For this reason, in long-lasting procedures and in the removal of large lesions, such as large flat polyps, repeated injection of the solution into the submucosal layer are required, with a consequent operational complication for the personnel of the endoscopic unit.

In order to overcome the fast disappearance of the cushion, which represents a typical problem encountered with NS, during the past decade several types of solutions have been described and tested for the use in solution-assisted EMR. Each type of solution has its advantages and disadvantages. For example, hyaluronic acid (HA) solutions have been reported as the best agents for submucosal injections. HA solutions provide long-lasting fluid cushions and allow high successful en-bloc resections and low perforation complication rates. Moreover, HA is safe, biocompatible and non-toxic, since it is a physiological component of the extracellular matrix. The main disadvantage of HA is its high cost, which renders it quite inaccessible for most endoscopic units. Other solutions have been tested and described, such hypertonic dextrose and hydroxypropyl methylcellulose (HPMC), which however have been reported to cause tissue damage and inflammation. Another recently investigated injection solution is fibrinogen mixture (FM) solution, which has a high viscosity and produces a long-lasting submucosal elevation, thus lowering the number of injections per lesion and shortening procedure times; in addition, FM is inexpensive. The main disadvantage of FM is the possible the risk of transmission of viruses: since FM is obtained by the fractionalization of coagulation proteins in human serum, contamination with hepatitis or other viruses is possible. As above illustrated, an ideal solution for EMR and ESD has not yet been developed, and many researches in this field are still on-going.

Ideally, viscous solutions such as HA solutions or HPMC solutions could meet the requirements of the endoscopic resection procedures, since they could provide a high and long-lasting cushion because of the low tendency of the water coordinated by these polymers to diffuse and spread out in the tissues surrounding the lesion. However, the use of viscous solutions, such as HA solutions or HPMC solutions, poses some challenges in the procedure, due to the difficulty to get a viscous solution flowed through the injection devices. As a matter of facts, in gastrointestinal EMR and ESD procedures, the injections of the cushion-forming solutions are performed using endoscopic injection needles. As well known in the art, endoscopic injection needles are devices which can be long up to about 230 cm and which include a relatively long catheter within which an inner injection tube having a distal injection needle is slideably disposed. A proximal actuating handle is coupled to the catheter and the injection tube for moving one relative to the other when necessary. Fluid access to the injection tube is typically provided via a luer connector on the handle. Endoscopic injection needle devices are typically delivered to the injection site through the working channel of the endoscope. In order to protect the lumen of the endoscope working channel from damage, the handle of the infusion needle device is manipulated to withdraw the distal injection needle into the lumen of the catheter before inserting the device into the endoscope. This is important to prevent exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length. After the injection site has been pierced, the solution, usually contained in a 5 mL to 10 mL syringe provided with a luer-lock fitting connected to the handle of the injection needle, is delivered through the injection tube and the needle into the injection site.

The injection needle and other accessories commonly used during endoscopic procedures, such as snares for polypectomy, clipping devices, biopsy forceps and similar, are passed through one or more specific channels of the endoscope, usually called working channels or operating channels. Depending upon the type of endoscope used in GI endoscopy (e.g. gastroscope, enteroscope, colonoscope, duodenoscope, sigmoidoscope and similar), the inner diameter of the working channels may vary considerably. However, the most common endoscopes used in GI endoscopy have working channels with inner diameter in the range from about 2 mm to about 5 mm. Generally, the manufacturers of endoscopic accessories produce accessories having outer diameters which allow them to fit all the working channels. In particular, as regards the endoscopic injection needles, the outer diameter of catheter ranges from 1.9 mm to 2.3 mm; thus, considering that the inner injection tube is contained in the outer catheter, its internal diameter is usually 1 mm or less. Such a small diameter of the injection tube causes a high dynamic resistance to the flowing of the solution; this is more valid and important when a viscous solution is used. For this reason, the viscous solutions used for EMRs and ESDs often need to be diluted before their use to make the solutions able to flow through the injection needle, with a loss of their characteristics of providing a high and long-lasting cushion. WO2011/103245 A1 describes a kit and a method for delivering a injectable solution to a tissue treatment site, for use in ESD. Said kit includes a housing having a chamber, a proximal portion and a distal portion. An injectable solution having a viscosity greater than about 10000 cP is provided in the chamber. The kit also includes a plunger movably positionable within the proximal portion of the chamber, the plunger provides a seal at the proximal end portion. A pressure gauge is also provided with the kit. A handle is connected to the housing and a plunger advancing member having a plunger handle is connected thereto. The plunger advancing member is provided separate from the housing and includes a distal portion configured for operably connecting with the proximal portion of the housing. The kit also includes an inner shaft provided separate from the housing and having a proximal end portion configured for operably connecting with the distal portion of the housing for receiving the injectable solution there through and a distal end configured for insertion in to the tissue treatment site. As a skilled in the art would recognize, such a device allows the physician to apply a pressure much higher than using a normal syringe, thus allowing the high viscous solution, having a viscosity of 10000 cP or greater, to flow into the injection tube. Furthermore, WO2011/103245 A1 discloses that suitable materials for inclusion in the injectable solution include methylcelluloses, such as carboxymethyl cellulose (CMC) and hydroxypropyl methylcellulose (HPMC), extracellular matrix proteins, elastin, collagen, gelatin, fibrin, agarose, and alginate or mixtures thereof. However, the use of such a "high-pressure" generating device during the endoscopic examination is known for being not favourably accepted by the experts of the field, since it is cumbersome, additional work is required to put it in place, it is difficult to be operated therefore it represents a complication of the EMR and ESD procedures.

Another tentative to overcome these issues is described in WO2009/070793 A1 which discloses the use of purified inverse thermosensitive polymers in EMR. As well known in the art, inverse thermosensitive polymers are polymers which, upon dissolution in solvents (such as water) in a concentration above the critical micellar concentration (CMC), have the tendency to form micelles. At concentrations higher than the critical gelation concentration (CGC), these micelles can order into a lattice; the result is a solution which shows inverse characteristics of viscosity, which means that said solution displays an increase of its viscosity with the temperature. Eventually, when the temperature is raised above the critical gelation temperature (CGT), a gel forms. The gelation is due to physical entanglement and packing of the micellar structures, and it is reversible, thus the gel turns back to a liquid form when temperature is lowered below the critical gelation temperature. Polymers of this kind are well known in the art, and comprise, for examples, poloxamers (commercialized by BASF under the brand name of Kolliphor™) and poloxamines (commercialized by BASF under the brand name of Tetronic™). Aqueous solutions of those polymers at concentrations above CGC can be liquid at room temperature and can form a gel once heated up to body temperature (i.e. about 37° C.). WO2009/070793 A1 discloses the use of a composition comprising a purified inverse thermosensitive polymer in an endoscopic procedure for gastrointestinal mucosal resectioning. Said composition, called LeGoo-endo™, is an aqueous solution of purified poloxamer 237; it is disclosed that the rapid reversible liquid to gel transition achieved as a result its purified nature allows LeGoo-endo™ to be liquid at room temperature and to become a gel only as it emerges from the catheter at the EMR site, once heated to body temperature. WO2009/070793 A1 teaches that, in order to obtain said rapid liquid to gel transition, the use of a purified poloxamer was needed, and that said purified poloxamer was obtained by a purification process aimed to the obtainment of a purified polymer characterized by a lower polydispersity of the molecular weight. Moreover, WO2009/070793 A1 discloses that it was necessary to develop a method of injecting through a catheter into the intestine or stomach a purified inverse thermosensitive polymer solution that transitions to a gel at body temperature. Among the challenges overcome was the fact that because the catheter quickly reaches body temperature while resident inside the body, the purified inverse thermosensitive polymer could gel inside the catheter prior to reaching the desired site for EMR. WO2009/070793 A1 discloses that the delivery problems were solved with a system comprising a high-pressure needle catheter connected to a syringe filled with purified inverse thermosensitive polymer solution, wherein said high-pressure needle catheter was contained within an administration device (e.g., a syringe pump) that generated pressure on the plunger of the syringe through a manual (e.g., screw), electrical or pressurized-gas mechanism. As a matter of facts, in the in vivo example, WO 2009/070793 A1 discloses that five EMR were performed in the colon of 2 pigs with LeGoo-endo™ using a 23-gauge scletotherapy needle with a 5-mL syringe and a balloon dilator gun; LeGoo-endo™ was kept on ice during the intervention. Saline containing syringes were also kept on ice to cool the catheter immediately before poloxamer injections. As a person skilled in the art will recognize, the operating procedure disclosed by WO2009/070793 A1 is quite complex, for the following reasons: it requires that the purified inverse thermosensitive polymer solution is kept on ice during the intervention; it requires the use of a particular, high-pressure needle catheter; it requires that, immediately before the injection of the purified inverse thermosensitive polymer solution, the catheter is cooled by means of injections of cold normal saline solution kept on ice; it requires an administration device (e.g., a syringe pump) that generates pressure on the plunger of the syringe to administer the purified inverse thermosensitive polymer solution.

U.S. Pat. No. 7,909,809 teaches a method for performing an interventional endoscopic procedure in the gastrointestinal tract such as polypectomy, endoscopic mucosal resection (EMR) and endoscopic submucosal dissection (ESD), said method comprising the administration to a human of a bulking or cushioning material that has characteristics of phase transition from a low viscosity state (e.g. liquid phase) into a high viscosity state (e.g. gel phase) in response to a predetermined temperature (e.g. body temperature).

As delineated above, an ideal composition for endoscopic mucosal resection (EMR) and endoscopic submucosal dissection (ESD) has not yet been developed. As reported above, compositions in form of solution containing, for example, HA (hyaluronic acid) are known in the art: HA (hyaluronic acid) solutions are viscous and capable of providing long-lasting submucosal cushions; moreover, they are safe and non toxic. However, they are known to be highly expensive.

Cellulose derivatives, such as HPMC and CMC, are cheap and their solutions are capable of providing long-lasting submucosal cushions; however, due to their viscosity, a particular device such as a syringe pump is required to make them flow into the injection needle, thus they are known for being difficult and uncomfortable to be injected.

Inverse thermosensitive polymers, such as poloxamers and poloxamines, are cheap and their solutions, in view of their capability of gelling at body temperature (i.e. about 37° C.), are capable of providing long-lasting submucosal cushions; it is however known in the art that, to obtain the gelification of the solution at body temperature (i.e. about 37° C.), such polymers need to be contained in the solution in a concentration equal to or above the critical gelation concentration (CGC), which is the concentration at which the transition of phase from solution to gel occurs upon heating at or above the critical gelation temperature (CGT). Accordingly, such polymers are usually contained in the known solutions in an amount equal to or above the critical gelation concentration (CGC). Similar concentrations of these polymers however cause several drawbacks, such as the gelification of the solution containing thereof inside the injection needle. A complex procedure is performed in order to avoid that the solution gelled inside the injection needle, namely keeping the composition on ice, cooling the injection needle with cold NS (normal saline solution) then using a syringe pump to administer them, with evident disadvantages for the endoscopist.

Therefore, there is the need to provide a composition for use in endoscopic procedure (particularly in EMR and ESD) able to be safe, inexpensive, non toxic, readily available, easy to inject and at the same time capable of providing a high, long-lasting submucosal cushion.

SUMMARY OF THE INVENTION

Figure 1:
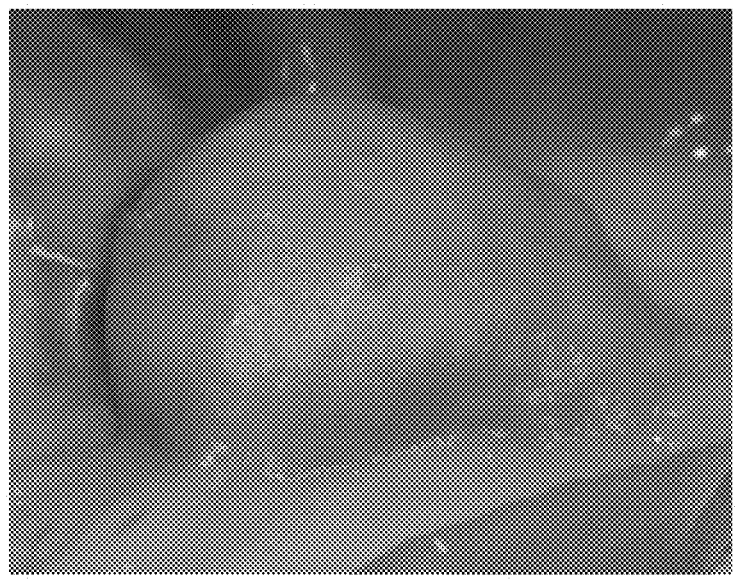
FIG. 1: The first cushion generated by the injection of the composition according to example 1 into the sub-mucosal layer of an ex-vivo porcine stomach.

The invention herein disclosed provides a pharmaceutical composition in form of emulsion or microemulsion and the use thereof in endoscopic procedures, preferably gastrointestinal endoscopic procedures.

The invention provides a pharmaceutical composition in form of emulsion or microemulsion for use in an endoscopic procedure, wherein said pharmaceutical composition comprises at least one inverse thermosensitive polymer and optionally at least one physiologically acceptable excipient. Preferably, said endoscopic procedure comprises the administration of said pharmaceutical composition to a human.

The invention herein disclosed provides a method for performing an endoscopic procedure, wherein said pharmaceutical composition comprises at least one inverse thermosensitive polymer and optionally at least one physiologically acceptable excipient. Preferably, said method comprises the administration of a pharmaceutical composition in form of emulsion or microemulsion to a human.

DESCRIPTION OF THE INVENTION

The invention herein disclosed provides a pharmaceutical composition in form of emulsion or microemulsion wherein said pharmaceutical composition comprises at least one inverse thermosensitive polymer in an amount below the critical gelation concentration (CGC) and wherein said pharmaceutical composition remains in liquid phase up to a temperature of about 40° C. in laboratory test conditions and the use thereof in endoscopic procedures. Preferably, said endoscopic procedures are gastrointestinal endoscopic procedures. More preferably, said gastrointestinal endoscopic procedures are performed in the esophagus, stomach and/or small intestine (duodenum, jejunum, ileum), in the cecum, in the colon, in the sigmoid colon and/or in the rectum.

The invention herein disclosed provides a pharmaceutical composition in form of emulsion or microemulsion for use in endoscopic procedures, wherein said pharmaceutical composition comprises at least one inverse thermosensitive polymer in an amount below the critical gelation concentration (CGC) and wherein said pharmaceutical composition remains in liquid phase up to a temperature of about 40° C. in laboratory test conditions.

The invention herein disclosed provides a method for performing an endoscopic procedure, said method comprising the administration of a pharmaceutical composition in form of emulsion or microemulsion to a human, wherein said pharmaceutical composition comprises at least one inverse thermosensitive polymer in an amount below the critical gelation concentration (CGC) and wherein said pharmaceutical composition remains in liquid phase up to a temperature of about 40° C. in laboratory test conditions.

According to the invention, said endoscopic procedure is preferably an endoscopic resection performed during a gastrointestinal endoscopy, more preferably a polypectomy, an endoscopic mucosal resection (EMR) and/or an endoscopic submucosal dissection (ESD).

According to the invention, said gastrointestinal endoscopy is preferably performed in the esophagus, stomach and/or small intestine (duodenum, jejunum, ileum), in the cecum, in the colon, in the sigmoid colon and/or in the rectum.

Further, the invention herein disclosed provides a kit for use in an endoscopic procedure, said kit comprising a pharmaceutical composition in form of emulsion or microemulsion, an endoscopic injection needle, a syringe and instruction for use thereof, wherein said pharmaceutical composition in form of emulsion or microemulsion comprises at least one inverse thermosensitive polymer and wherein said endoscopic procedure is preferably an endoscopic resection of the mucosa performed during a gastrointestinal endoscopy, more preferably a polypectomy, an endoscopic mucosal resection (EMR) and/or an endoscopic submucosal dissection (ESD).

More in details, the pharmaceutical composition in form of emulsion or microemulsion is injected in a target tissue in order to form a cushion, which may be then optionally subjected to an endoscopic surgical procedure, such as a resection procedure.

All publications, patents and patent applications cited herein, whether supra or infra, are hereby incorporated by reference in their entirety.

DETAILED DESCRIPTION OF THE INVENTION

The inventors have been working to find out innovative pharmaceutical compositions for use in endoscopic procedures, preferably polypectomy, endoscopic mucosal resection (EMR) and/or endoscopic mucosal resection (ESD) which embodies the characteristics requested by endoscopic physicians, especially safety, inexpensiveness, absence of toxic effects, easiness to be injected and capacity of providing a high, long-lasting sub-mucosal cushion.

It was surprisingly discovered that pharmaceutical compositions in form of emulsions or microemulsions which comprise at least one inverse thermosensitive polymer in an amount below the critical gelation concentration (CGC) and remain in liquid phase up to a temperature of about 40° C. in laboratory test conditions, show the ability to form a high, long-lasting sub-mucosal cushion being meanwhile safe, inexpensive, non toxic and easy to be injected. It is therefore clear the consequent improvement given by these compositions in endoscopic procedures, particularly in the endoscopic resection during gastrointestinal endoscopy.

The high, long-lasting submucosal cushion has been surprisingly observed by the inventors once the composition in form of emulsion or microemulsion according to the invention herein disclosed was injected into the submucosal layer of an ex vivo porcine stomach, which constitutes a well known model of the human gastrointestinal mucosa (Soo Hoon Eun et al. "Effectiveness of Sodium Alginate as a Submucosal Injection Material for Endoscopic Mucosal Resection in Animal", Gut and Liver, Vol. 1, No 1, June 2007, pp 27-32).

As well known in the art, inverse thermosensitive polymers are polymers which, upon dissolution in water in a concentration above the critical gelation concentration (CGC), provide solutions that show inverse characteristics of viscosity, which means that said solutions display an increase of their viscosity with the temperature. In particular, aqueous solutions of said polymers form gels above the critical gelation concentration (CGC), when the temperature is raised above the critical gelation temperature (CGT). The gelation is due to physical entanglement and packing of the micellar structures, and it is reversible, thus the gel turns back to a liquid form when temperature is lowered below the critical gelation temperature. Polymers of this kind are well known in the art, and comprise, for examples, poloxamers (commercialized by BASF under the brand name of Kolliphor™) and poloxamines (commercialized by BASF under the brand name of Tetronic™). As well known in the art, each kind of poloxamer has a characteristic critical gelation concentration (CGC); among the poloxamers, poloxamer 407 has the lowest CGC. As reported in Evren Algin Yapar et al., Tropical Journal of Pharmaceutical Research October 2012; 11 (5): 855-866, in order to attain relatively stable gels, these applications require polymer concentrations of usually equal to or above 15% by weight, with respect to the weight of the solution. Moreover, J. J. Escobar-Chavez et al., Journal of Pharmacy & Pharmaceutical Sciences, 9(3):339-358, (2006) reports that poloxamer 407 is of particular interest since concentrated solutions (>20% w/w) of the copolymer are transformed from low viscosity transparent solutions to solid gels on heating to body temperature. As already mentioned, aqueous solutions of said polymers form gels above the critical gelation concentration (CGC), when the temperature is raised above the critical gelation temperature (CGT). The critical gelation temperature (CGT) can be modulated by varying the concentration of the inverse thermosensitive polymer, which means that the higher the concentration of said polymer, the lower the critical gelation temperature (CGT). As well known in the art, the gel-forming ability of solutions of inverse thermosensitive polymers requires that the concentration of said polymers in said solutions is equal to or above the critical gelation concentration (CGC): if such polymers are contained in an amount below the CGC, the solutions do not transition from a liquid phase to a gel phase in response to the raise in temperature. At the time the invention was made, it was thought in the art that the ability to form a gel upon heating to body temperature (i.e. about 37° C.) in laboratory test conditions characteristic of aqueous solutions containing some kinds of inverse thermosensitive polymers in an amount equal to or above the critical gelation concentration (CGC), was an essential feature for ensuring the formation of a long-lasting submucosal cushion once said solutions were injected into the submucosal layer of the gastrointestinal tract. As a matter of facts, it was thought that said solutions were able to form a long-lasting submucosal cushion upon injection into the submucosal layer of the gastrointestinal tract due to the transition to a gel phase, in response to the raise in the temperature (i.e. the body temperature). Thus, it was thought in the art that the ability of aqueous solutions containing an inverse thermosensitive polymer in an amount equal to or above the critical gelation concentration (CGC) to form a long-lasting submucosal cushion upon injection into the submucosal layer of the gastrointestinal tract was bound to their ability to gel upon heating at body temperature (i.e. about 37° C.) in laboratory test conditions. In other words, it was thought that, in order to ensure the formation of a long-lasting cushion into the submucosal layer of the gastrointestinal tract, said solutions had to contain an inverse thermosensitive polymer at a concentration equal to or above the critical gelation concentration (CGC), since only in this case said solutions would have been able to transition from a liquid phase to a gel phase in response to the raise in temperature (e.g. the body temperature).

It was now discovered that pharmaceutical compositions in form of emulsions or microemulsions according to the invention herein disclosed, which do not have the ability to form a gel (i.e. remain in a liquid phase) up to a temperature of about 40° C. in laboratory test conditions, preferably upon heating at body temperature (i.e. about 37° C.), are surprisingly able to form a high, long-lasting submucosal cushion once injected into the submucosal layer of a porcine stomach (ex-vivo). In particular, in a comparison test foreseeing the injection of different compositions into the submucosal layer of a porcine stomach maintained at a temperature of about 37° C., it was surprisingly discovered that pharmaceutical compositions in form of emulsions or microemulsions according to the invention herein disclosed, even though unable to gel upon heating at body temperature (i.e. about 37° C.) in laboratory test conditions, were surprisingly able to form a high, long-lasting cushion in the above submucosal layer (porcine stomach ex-vivo) similar for height, shape and duration to that formed by conventional solutions, i.e. comprising an inverse thermosensitive polymer at a concentration above the critical gelation concentration which were able to gel upon heating at body temperature (i.e. about 37° C.) in laboratory conditions.

It was therefore surprisingly discovered that the absence of gelling properties, observed in laboratory test conditions for the pharmaceutical compositions in form of emulsions or microemulsions according to the invention herein disclosed, was not related to the ability of forming a submucosal cushion of said pharmaceutical compositions observed in the porcine stomach (ex-vivo). As a person skilled in the art will recognize, such results were unexpected and unobvious as well as of significant advantage in the endoscopic procedures. In the known art, it was in fact taught that the gel-forming ability of solutions of inverse thermosensitive polymers upon heating at body temperature (i.e. about 37° C.), in laboratory conditions, was related to the gel-forming ability of said solutions in ex-vivo or in in-vivo models of gastrointestinal mucosal resectioning procedures.

The inventors have surprisingly found that the pharmaceutical compositions in form of emulsions or microemulsions according to the invention herein disclosed have the ability of forming a submucosal cushion in ex vivo and/or in in vivo models of gastrointestinal mucosal resectioning procedures, even though the inverse thermosensitive polymer concentration is contained in said pharmaceutical compositions in an amount below its critical gelation concentration (CGC) and, consequently, said pharmaceutical compositions are unable to gel up to a temperature of about 40° C., especially upon heating at body temperature (i.e. about 37° C.), in laboratory test conditions.

The invention herein disclosed provides a pharmaceutical composition in form of emulsion or microemulsion, wherein said pharmaceutical composition comprises at least one inverse thermosensitive polymer in an amount below the critical gelation concentration (CGC) and wherein said pharmaceutical composition remains in liquid phase up to a temperature of about 40° C. in laboratory test conditions and the use thereof in endoscopic procedures.

The invention herein disclosed provides a pharmaceutical composition in form of emulsion or microemulsion for use in an endoscopic procedure, wherein said composition comprises at least one inverse thermosensitive polymer in an amount below the critical gelation concentration (CGC), and wherein said composition remains in liquid phase up to a temperature of about 40° C. in laboratory test conditions.

According to the invention, said endoscopic procedure comprises the administration of said pharmaceutical composition to a human.

According to the invention said endoscopic procedure is preferably a gastrointestinal endoscopic procedure, more preferably performed in the esophagus, stomach, small intestine (duodenum, jejunum, ileum), in the cecum, in the colon, in the sigmoid colon and/or in the rectum.).

More in details, the pharmaceutical composition is injected in a target tissue of said human in order to form a cushion which is then optionally subjected to an endoscopic surgical procedure, such as a resection procedure, The invention herein disclosed thus provides also a method for performing an endoscopic procedure, said method comprising the administration of a pharmaceutical composition in form of emulsion or microemulsion to a human, wherein said composition comprises at least one inverse thermosensitive polymer in an amount below the critical gelation concentration (CGC), and wherein said composition remains in liquid phase up to a temperature of about 40° C. in laboratory test conditions. More in details, the pharmaceutical composition is injected in a target tissue of said human in order to form a cushion which is then optionally subjected to an endoscopic surgical procedure, such as a resection procedure.

According to the invention, the pharmaceutical composition in form of emulsion or microemulsion preferably remains in liquid phase at a temperature comprised between about 5° C. and 40° C., more preferably at about 5° C., about 20° C., about 25° C., about 30° C. and/or about 37° C. in laboratory test conditions.

According to a preferred embodiment of the invention, the pharmaceutical composition in form of emulsion or microemulsion remains in liquid phase both at room temperature (i.e. about 20-25° C.) and at body temperature (i.e. about 37° C.) in laboratory test conditions.

According to another preferred embodiment, the pharmaceutical composition in form of emulsion or microemulsion of the invention has a viscosity below about 150 cP (centipoises), more preferably below about 100 cP (centipoises), much more preferably below about 50 cP (centipoises). According to another preferred embodiment the pharmaceutical composition in form of emulsion or microemulsion of the invention has a viscosity below about 20 cP (centipoises), more preferably below about 10 cP. According to the invention, said viscosity is preferably measured at about 25° C., at about 30° C. and/or at about 37° C., more preferably using a Brookfield LVDV-III Ultra Programmable Rheometer™ equipped with a Brookfield Small Sample Adapter™ device and using a Brookfield™ spindle N. 31. Alternatively, said viscosity is measured using a Brookfield LVDV-III Ultra Programmable Rheometer™ equipped with a Brookfield Enhanced UL Adapter™ device and using a Brookfield™ spindle N. 00.

According to another preferred embodiment of the invention, said endoscopic procedure is an endoscopic resection procedure performed during a gastrointestinal endoscopy, preferably a polypectomy, an endoscopic mucosal resection (EMR) and/or an endoscopic submucosal dissection (ESD).

According to the invention said endoscopic procedure is preferably a gastrointestinal endoscopic procedure, more preferably performed in the esophagus, stomach, small intestine (duodenum, jejunum, ileum), in the cecum, in the colon, in the sigmoid colon and/or in the rectum.

According to the invention, said polypectomy, endoscopic mucosal resection (EMR) and/or said endoscopic submucosal dissection (ESD) are used for the removal of mucosal lesions, polyps, pseudo-polyps, flat polyps, adenomas, serrated lesions, dysplasias, Barrett's dysplasia, pre-neoplastic formation, neoplastic formations and/or tumors during gastrointestinal endoscopy.

According to the invention, said polypectomy, endoscopic mucosal resection (EMR) and/or said endoscopic submucosal dissection (ESD) are also used for the removal of pathologic and/or dysplastic mucosal tissue in case of esophagitis, erosive esophagitis, Barrett's esophagus (such as in ablation procedures), and/or gastrointestinal pathological hypersecretory conditions, such as Zollinger Ellison Syndrome.

According to an embodiment, said pharmaceutical composition in form of emulsion or microemulsion is administered to a human through injection by means of an endoscopic injection needle provided with a retractable needle and of a syringe.

According to the invention, said pharmaceutical composition in form of emulsion or microemulsion can be preferably a water-in-oil emulsion or microemulsion, or an oil-in-water emulsion or microemulsion. According to a preferred embodiment, the pharmaceutical composition in form of emulsion or microemulsion is an oil-in-water emulsion or microemulsion.

According to an embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer,
(e) optionally at least one physiologically acceptable excipient;
wherein said at least one inverse thermosensitive polymer is comprised in an amount below the critical gelation concentration (CGC), and wherein said composition is in liquid phase up to a temperature of about 40° C. in laboratory test conditions.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) optionally at least one physiologically acceptable excipient;
wherein said at least one inverse thermosensitive polymer is comprised in an amount below the critical gelation concentration (CGC), and wherein said composition is in liquid phase up to a temperature of about 40° C. in laboratory test conditions.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) at least one dye;
(g) optionally at least one physiologically acceptable excipient;
wherein said at least one inverse thermosensitive polymer is comprised in an amount below the critical gelation concentration (CGC), and wherein said composition is in liquid phase up to a temperature of about 40° C. in laboratory test conditions.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) at least one dye;
(g) optionally at least one agent characterized by having a trophic activity on the epithelial cells of the gastrointestinal mucosa;
(h) optionally at least one physiologically acceptable excipient;
wherein said at least one inverse thermosensitive polymer is comprised in an amount below the critical gelation concentration (CGC), and wherein said composition is in liquid phase up to a temperature of about 40° C. in laboratory test conditions.

According to another embodiment, said pharmaceutical composition in form of emulsion or microemulsion for use in an endoscopic procedure comprises:
(a) an aqueous phase;
(b) an oily phase;
(c) at least one surfactant;
(d) at least one inverse thermosensitive polymer;
(e) optionally at least one co-surfactant;
(f) at least one dye;
(g) optionally at least one agent characterized by having a trophic activity on the epithelial cells of the gastrointestinal mucosa;
(h) optionally at least one therapeutic agent;
(i) optionally at least one physiologically acceptable excipient;
wherein said at least one inverse thermosensitive polymer is comprised in an amount below the critical gelation concentration (CGC), and wherein said composition is in liquid phase up to a temperature of about 40° C. in laboratory test conditions.

According to another embodiment, the present invention relates to a pharmaceutical composition in form of emulsion or microemulsion which comprises, consists or essentially consists of:
(a) an aqueous phase;
(b) an oily phase;
(c) at least one surfactant;
(d) at least one inverse thermosensitive polymer,
(e) optionally at least one co-surfactant;
(f) optionally at least one dye;

(g) optionally at least one agent characterized by having a trophic activity on the epithelial cells of the gastrointestinal mucosa;
(h) optionally at least one therapeutic agent;
(i) optionally at least one physiologically acceptable excipient;

wherein said at least one inverse thermosensitive polymer is comprised in an amount below the critical gelation concentration (CGC), and wherein said composition is in liquid phase up to a temperature of about 40° C. in laboratory test conditions.

According to the invention, the pharmaceutical composition in form of emulsion or microemulsion preferably remains in liquid phase at a temperature comprised between about 5° C. and about 40° C., more preferably at about 5° C. and/or about 20° C. and/or about 25° C. and/or about 30° C. and/or about 37° C., in laboratory test conditions.

According to the invention herein disclosed, the main component of the aqueous phase of said pharmaceutical composition is water for injection. As well known in the art, water for injection represents a highly purified, distilled water, free of salts and of carbon contaminants, and free of microorganisms and of bacterial endotoxins. Water for injection is water purified by distillation or a purification process that is equivalent or superior to distillation in the removal of chemicals and of microorganisms. In some embodiments of the invention herein disclosed, said aqueous phase may comprise, in dissolved form, one or more inorganic salts selected form the group comprising, but not limited to: chlorides, bromides, iodides, phosphates, carbonates, bicarbonates, sulfates, nitrates and the like. In some embodiments, said aqueous phase may comprise, in dissolved form, one or more organic salts selected form the group comprising, but not limited to: citrates, maleates, fumarates, acetates, lactates and the like. Any mixture of the above inorganic and organic salts may be used to form the appropriate pharmaceutical composition, generally to buffer the pH of the composition in suitable biocompatible ranges or to reach the osmotic pressure required by the biologic environment where said pharmaceutical composition has to be injected. In some embodiments, the aqueous phase of the pharmaceutical composition herein disclosed may comprise an amount of one or more inorganic and/or organic salts or mixtures thereof such as to have a final pharmaceutical composition which is hypotonic. In some embodiments, the aqueous phase of the pharmaceutical composition herein disclosed may comprise an amount of one or more inorganic and/or organic salts or mixtures thereof such as to have a final pharmaceutical composition which is isotonic. In some embodiments, the aqueous phase of the pharmaceutical composition herein disclosed may comprise an amount of one or more inorganic and/or organic salts or mixtures thereof such as to have a final pharmaceutical composition which is hypertonic. According to the invention herein disclosed, said inorganic and/or organic salts or mixtures thereof may be present in an amount ranging from 0% to 5% by weight with respect to the weight of the composition, more preferably from 0.1% to 4% by weight with respect to the weight of the composition, much more preferably from 0.5% to 3% by weight with respect to the weight of the composition. According to a preferred embodiment, said inorganic and/or organic salts or mixtures thereof may be present in an amount ranging from 0.3% to 0.7% by weight respect to the weight of the composition.

In a preferred embodiment, the aqueous phase of said pharmaceutical composition contains sodium chloride dissolved. According to the latter embodiment, said sodium chloride is present in an amount ranging from about 0% to about 5% by weight with respect to the weight of the composition, more preferably from about 0.1% to about 3% by weight with respect to the weight of the composition, much more preferably from about 0.5% to about 2% by weight with respect to the weight of the composition.

According to a preferred embodiment, said sodium chloride may be present in an amount ranging from 0.3% to 0.7% by weight respect to the weight of the composition. More preferably, said sodium chloride is present in an amount of about 0.44% w/w.

In some embodiments, the aqueous phase of the pharmaceutical composition herein disclosed comprises a buffer. In some embodiments, said buffer is a phosphate buffer. In some embodiments, said buffer is a citrate buffer. In some embodiments, said buffer is a bicarbonate buffer. In a preferred embodiment, said buffer is a phosphate buffer added with one or more inorganic salts unable to buffer the pH. According to the latter embodiment, the concentration of said phosphate buffer and said inorganic salts unable to buffer the pH is such as to have an aqueous phase which is phosphate buffered saline (PBS). As well known in the art, PBS is a water-based salt solution containing sodium chloride, sodium phosphate, and, optionally, potassium chloride and potassium phosphate; PBS for medical applications is an isotonic solution, i.e. its osmolarity and its pH match those of the human body. Several compositions and preparation methods of PBS are well known in the art.

According to the invention herein disclosed, the pH value of the pharmaceutical composition in form of emulsion or microemulsion ranges from about 4.0 to about 9.0, more preferably from about 5.0 to about 8.0, much more preferably from about 5.5 to about 7.5. According to the invention, the pH value of said pharmaceutical composition in form of emulsion or microemulsion may be adjusted within the desired range by common techniques well known in the art, such as, for example, the addition of physiologically acceptable bases and/or acids.

According to the invention herein disclosed, said oily phase of said pharmaceutical composition comprises at least one lipophilic compound. In some embodiments, said at least one lipophilic compound may be selected in the group of natural oils, comprising, but not limited to: almond oil, canola oil, castor oil, corn oil, cottonseed oil, olive oil, safflower oil, sesame oil, soybean oil and the like. In some embodiments, said at least one lipophilic compound may be selected in the group of fatty acid esters, comprising, but not limited to: isopropyl palmitate, isopropyl myristate, ethyl oleate and the like. In some embodiments, said at least one lipophilic compound may be selected in the group of fatty alcohols, comprising, but not limited to: myristic alcohol, oleyl alcohol and the like. In some embodiments, said at least one lipophilic compound may be selected in the group of fatty acids, comprising, but not limited to: myristic acid, oleyl acid, palmitic acid and the like. In some embodiments, said at least one lipophilic compound may be selected in the group of triglycerides, such as long and/or medium-chain triglycerides and the like. In some embodiments, said at least one lipophilic compound may be selected in the group of diglycerides. In some embodiments, said at least one lipophilic compound may be selected in the group of monoglycerides. Any mixture of the above lipophilic compounds can be used to form the appropriate pharmaceutical composition. In one embodiment, the lipophilic compound of said oily phase is sesame oil. In another embodiment, the lipophilic compound of said oily phase is almond oil. In another embodiment, the lipophilic compounds of said oily phase are medium-chain triglycerides. In a preferred embodiment, the lipophilic compound of said oily phase is soybean oil.

According to the invention herein disclosed, the oily phase of said pharmaceutical composition ranges from about 0.001% to about 20% by weight with respect to the weight of the composition, preferably from about 0.01% to about 2% by weight with respect to the weight of the composition, more preferably from about 0.02% to about 1% by weight of the with respect to the weight of the composition. According to a preferred embodiment, said oily phase is contained in the composition of the invention in an amount from about 0.01% by weight to about 0.5% by weight, with respect to the weight of the composition.

More preferably, the oily phase is contained in the composition of the invention in an amount of about 0.08% by weight or about 0.16% by weight, with respect to the weight of the composition. Much more preferably, said oily phase is contained in the composition of the invention in an amount of about 0.02% w/w or about 0.05% w/w or about 0.1% by weight, with respect to the weight of the composition. According to the invention herein disclosed, the pharmaceutical composition in form of emulsion or microemulsion contains at least one inverse thermosensitive polymer at a concentration below the critical gelation concentration (CGC). Accordingly, said pharmaceutical composition in form of emulsion or microemulsion is not able to transition from a liquid phase to a gel phase in response to the raise in temperature up to 40° C. in laboratory test conditions, such as from room temperature (i.e. about 20-25° C.) to body temperature (i.e. about 37° C.). Thus, said pharmaceutical composition in form of emulsion or microemulsion according to the invention herein disclosed is in liquid phase up to a temperature of about 40° C., preferably both at room temperature (i.e. about 20-25° C.) and at body temperature (i.e. about 37° C.) in laboratory test conditions. Each type of inverse thermosensitive polymer is characterized by a specific critical gelation concentration (CGC); such concentrations are well known in the art and can be easily found in scientific literature. According to the invention herein disclosed, said at least one inverse thermosensitive polymer may be selected in the group comprising, but not limited to: polyoxyethylene-polyoxypropylene block copolymers, such as poloxamers and the like. Said poloxamer may be selected in the group comprising, but not limited to: poloxamer 124, poloxamer 188, poloxamer 237, poloxamer 338, poloxamer 407 and the like. Any mixture of the above inverse thermosensitive polymers can be used to form the appropriate pharmaceutical composition. In a preferred embodiment, said at least one inverse thermosensitive polymer of said pharmaceutical composition is poloxamer 188. In a preferred embodiment, said at least one inverse thermosensitive polymer of said pharmaceutical composition is poloxamer 407. Further in another preferred embodiment, said at least one inverse thermosensitive polymer is a mixture of poloxamer 188 and poloxamer 407.

According to the invention, useful inverse thermosensitive polymers are bought on the market and used without any purification step.

According to the invention herein disclosed, said at least one inverse thermosensitive polymer is present in an amount below the critical gelation temperature (CGC), preferably below about 15% by weight with respect to the weight of the pharmaceutical composition, more preferably between about 2% and about 14.5% by weight with respect to the weight of the pharmaceutical composition, much more preferably between about 3% and about 12% by weight with respect to the weight of the pharmaceutical composition, further much more preferably between about 5% and about 11% by weight with respect to the weight of the pharmaceutical composition. Preferably, said at least one inverse thermosensitive polymer is present in an amount of about 7%, or about 8%, or about 9%, or about 10% by weight with respect to the weight of the composition.

According to an embodiment, said at least one inverse thermosensitive polymer is poloxamer 407 and it is contained in an amount of about 9% by weight with respect to the weight of the composition.

According to another embodiment, said at least one inverse thermosensitive polymer is poloxamer 188 and it is contained in an amount of about 10% by weight with respect to the weight of the composition.

According to a further preferred embodiment, said at least one inverse thermosensitive polymer is a mixture of poloxamer 188 and poloxamer 407, and such a mixture is contained in an amount of about 10% by weight with respect to the weight of the composition.

According to the invention herein disclosed, said at least one surfactant may be selected in the group of the non-ionic surfactants, comprising, but not limited to: PEG-fatty acid monoesters surfactants, such as PEG-15 hydroxystearate, PEG-30 stearate, PEG-40 laurate, PEG-40 oleate and the like; PEG-fatty acid diesters surfactants, such as PEG-32 dioleate, PEG-400 dioleate and the like; polyoxyethylene sorbitan fatty acid esters, such as polysorbate 20, polysorbate 60, polysorbate 80 and the like; polyoxyethylene alkyl ethers, such as PEG-20 cetostearyl ether, polyoxyl 25 cetostearyl, cetomacrogol 1000 and the like; sorbitan fatty acid esters surfactants, such as sorbitan monolaurate, sorbitan monopalmitate, sorbitan monooleate, and the like; propylene glycol esters of fatty acids; polyglycerol esters of fatty acids; polyoxyethylene castor oil derivatives such as polyoxyl 5 castor oil, polyoxyl 15 castor oil, polyoxyl 35 castor oil, polyoxyl 40 hydrogenated castor oil and the like; caprylocapryl polyoxyil-8 glycerides; polyoxylglycerides such as caprylocaproyl polyoxylglycerides, lauroyl polyoxylglycerides, oleoyl polyoxylglycerides and the like ceteareth 16, ceteareth 20, stearaeth 10, steareth 20, ceteth 20 and the like. Any mixture of the above non-ionic surfactant can be used to form the appropriate pharmaceutical composition. In one embodiment, the non-ionic surfactant is polysorbate 80. In a preferred embodiment, the non-ionic surfactant is PEG-15 hydroxystearate (also known as polyoxyl-15-hydroxystearate).

According to the invention herein disclosed, said at least one surfactant may be selected in the group of the ionic surfactants, comprising, but not limited to: egg lecithin, hydrogenated phosphatidyl choline from egg lecithin, soybean lecithin, hydrogenated soybean lecithin, glycerophosphocholine, soybean lysolecithin, phospholipids, hydrogenated phospholipids, sodium lauryl sulphate and the like. Any mixture of the above ionic surfactant can be used to form the appropriate pharmaceutical composition. The above ionic surfactants are commercialized by Lipoid, under the brand-name of Lipoid®. In one embodiment, the ionic surfactant is egg lecithin. In another embodiment, the ionic surfactant is hydrogenated phosphatidyl choline from egg lecithin. In another embodiment, the ionic surfactant is soybean lecithin. Further in another embodiment, the ionic surfactant is hydrogenated soybean lecithin.

According to the invention herein disclosed, said at least one surfactant is contained in an amount which ranges from about 0.001% to about 10% by weight with respect to the weight of the pharmaceutical composition, preferably from about 0.005% to about 5% by weight with respect to the weight of the pharmaceutical composition, more preferably from about 0.01% to about 2% by weight with respect to the weight of the pharmaceutical composition. According to a preferred embodiment, said at least one surfactant is contained in an amount of about 0.08% or about 0.1% or about 0.5% or about 0.6%, by weight with respect to the weight of the pharmaceutical composition.

The pharmaceutical composition of the invention herein disclosed may comprise at least one co-surfactant. The addition of at least one co-surfactant to the mixture oily phase-surfactant-aqueous phase is advantageous since the co-surfactant acts in synergy with the surfactant in lowering the interfacial tension of the droplets of the dispersed phase of the emulsion or microemulsion, with a stabilizing effect on the system. In the preparation of pharmaceutical compositions in form of emulsions or microemulsions according to the invention herein disclosed, said at least one co-surfactant can be selected in the groups comprising, but not limited to: low and medium chain alcohols, such as ethanol, propanol, isopropanol and the like; glycols, such as propylene glycol and the like; polyethylene glycols, such as PEG 200, PEG 300, PEG 400 and the like; DMSO; long chain alcohols, such as cetyl alcohol, myristyl alcohol, oleyl alcohol and the like; glycerol; low chain esters, such as ethyl acetate, ethyl lactate and the like; fatty acid esters, such as ethyl oleate, isopropyl myristate, isopropyl palmitate and the like; fatty acids, such as oleic acid, myristic acid and the like; salts of fatty acids, such as sodium oleate, sodium palmitate, sodium stearate and the like. Any mixture of the above co-surfactants can be used to form the appropriate pharmaceutical composition. In one embodiment, the co-surfactant is propylene glycol. In another embodiment, the co-surfactant is glycerol. In another embodiment, the co-surfactant is sodium oleate. In a preferred embodiment, the co-surfactant is a mixture of glycerol and sodium oleate.

According to the invention herein disclosed, said at least one co-surfactant is contained in an amount which ranges from about 0.00001% to about 1% by weight with respect to the weight of the pharmaceutical composition, preferably from about 0.00005% to about 0.05% by weight with respect to the weight of the pharmaceutical composition, more preferably from about 0.0001% to about 0.01% by weight with respect to the weight of the pharmaceutical composition.

The pharmaceutical composition of the invention herein disclosed may comprise at least one dye. Dyes are widely used in compositions for endoscopic procedures. In particular, in compositions for EMR and/or ESD procedures, the dyes are useful to feature the margins of the lesion to be resected and the physiological structures underlying the mucosa; thus, the endoscopist can easily visualize the lesion he has to remove and he can perform the procedure with less risks of damaging the submucosal layer or the muscular tissue. The dye has the function to render immediately visible to the endoscopist the submucosal layer, so that the surgical procedure is safer and there is a lower risk of damaging the structures beneath the mucosa, such as the submucosal layer itself and the external muscular wall.

In the preparation of the pharmaceutical composition according to the invention herein disclosed, said at least one dye may be selected among vital dyes (or absorptive dyes), non-vital dyes (or contrast dyes), and reactive dyes. Vital (or absorptive) dyes, such as Lugol's solution and methylene blue, identify specific epithelial cell types by preferential absorption or diffusion across the cell membrane; non-vital (or contrast) dyes, such as indigo carmine, seep through mucosal crevices and highlight surface topography and mucosal irregularities; reactive dyes, such as congo red and phenol red, undergo chemical reactions with specific cellular constituents, resulting in a colour change akin to a pH indicator. According to the invention herein disclosed, said vital (or absorptive) dye may be selected in the group comprising, but not limited to: Lugol's solution, methylene blue, toluidine blue, crystal violet and the like. According to the invention herein disclosed, said non-vital (or contrast) dye may be selected in the group comprising, but not limited to: indigo carmine and the like. According to the invention herein disclosed, said reactive dye may be selected in the group comprising, but not limited to: Congo red, phenol red and the like. Any mixture of the above dyes can be used to form the appropriate pharmaceutical composition. According to a preferred embodiment, said at least one dye is methylene blue. According to another preferred embodiment, said at least one dye is indigo carmine.

According to the invention herein disclosed, said at least one dye is contained in an amount which ranges from about 0.0001% to about 0.2% by weight with respect to the weight of the pharmaceutical composition, preferably from about 0.0002% to about 0.05% by weight with respect to the weight of the pharmaceutical composition, more preferably from about 0.0005% to about 0.01% by weight with respect to the weight of the pharmaceutical composition. Much more preferably, said at least one dye is contained in the composition of the invention in an amount of about 0.001% by weight or about 0.002% by weight, with respect to the weight of the composition.

The pharmaceutical composition of the invention herein disclosed may comprise at least one agent characterized by having a trophic activity on the epithelial cells of the gastrointestinal mucosa. Trophic agents are substances capable of promoting cellular growth, differentiation, and survival. In gastrointestinal endoscopy, resectioning procedures such as polypectomy, EMR and/or ESD are generally not followed by suturing. In other words, once the lesion has been removed by means of one of said procedures, the mucosa is not sutured and the wound is left opened; thus the healing of the wound must occur naturally. In this sense, the incorporation into the pharmaceutical compositions according to the invention of at least one agent proved to possess a trophic activity on the epithelial cells of the gastrointestinal mucosa could be advantageous, since said pharmaceutical compositions could exert a positive, beneficial effect on wound healing, promoting cellular growth and differentiation for a faster closure and healing of the surgical wound.

In the preparation of pharmaceutical compositions in form of emulsions or microemulsions according to the invention herein disclosed, said at least one agent characterized by having a trophic activity on the epithelial cells of the gastrointestinal mucosa can be selected in the groups comprising, but not limited to: aminoacids and salts thereof, such as arginine, glutamine, glutamic acid, citrulline, proline, cysteine and the like; short-chain fatty acids (SCFA) and salts thereof, such as acetic acid and salts thereof, propanoic acid and salts thereof, butyric acid and salts thereof, and the like; carbohydrates, such as glucose, fructose, galactose, sucrose, maltose, lactose and the like; polyamines and salts thereof, such as putresceine, spermidine, spermine and the like; fatty acids and salts thereof, such as oleic acid and salts thereof, linoleic acid and salts thereof, mirystic acid and salts thereof, stearic acid and salts thereof and the like; vitamins, such as vitamin A, vitamin $B_2$, vitamin C, vitamin D, and the like. Any mixture of the above agents characterized by having a trophic activity on the epithelial cells of the gastrointestinal mucosa can be used to form the appropriate pharmaceutical composition. In one embodiment, the at least one agent characterized by having a trophic activity on the epithelial cells of the gastrointestinal mucosa is sodium butyrate. In another embodiment, the at least one agent characterized by having a trophic activity on the epithelial cells of the gastrointestinal mucosa is sodium vitamin $B_2$. In a preferred embodiment, the at least one agent characterized by having a trophic activity on the epithelial cells of the gastrointestinal mucosa is glutamic acid.

According to the invention herein disclosed, said at least one agent characterized by having a trophic activity on the epithelial cells of the gastrointestinal mucosa is contained in an amount which ranges from about 0.01% to about 5% by weight with respect to the weight of the pharmaceutical composition, preferably from about 0.05% to about 3% by weight with respect to the weight of the pharmaceutical composition, more preferably from about 0.1% to about 2% by weight with respect to the weight of the pharmaceutical composition.

The pharmaceutical composition of the invention herein disclosed may comprise at least one therapeutic agent. In the preparation of pharmaceutical compositions in form of emulsions or microemulsions according to the invention herein disclosed, said at least one therapeutic agent can be selected in the groups comprising, but not limited to: antibiotics, such as penicillins, cephalosporins, aminoglycosides, macrolides, rifamycins, metronidazole and the like; non-steroidal anti-inflammatory drugs, such as ketorolac and salts thereof, indometacin, piroxicam, ketoprofen and salts thereof, and metamizol and salts thereof, and the like; steroidal anti-inflammatory drugs, such as cortisol, prednisolone and esters thereof, methyprednisolone and esters thereof, triamcinolone acetonide, betamethasone and esters thereof, and the like; local anesthetics, such as lidocaine and salts thereof, mepivacaine and salts thereof, bupuvacaine and salts thereof, and the like; vasoconstrictor drugs, such as epinephrine and salts thereof, norepinephrine and salts thereof, and the like. Any mixture of the above therapeutic agents can be used to form the appropriate pharmaceutical composition and to achieve specific therapeutic effects. In an embodiment, said at least one therapeutic agent is a local anesthetic, such as lidocaine hydrochloride. In another embodiment, said at least one therapeutic agent is a vasoconstrictor drug, such as epinephrine hydrochloride. Further in another embodiment, the pharmaceutical composition according to the invention herein disclosed comprises a local anaesthetic and a vasoconstrictor drug, such as lidocaine hydrochloride and epinephrine hydrochloride.

Additionally, at least one physiologically acceptable excipient may be added to the pharmaceutical composition according to the invention herein disclosed to obtain final composition for use in endoscopic procedures provided with suitable characteristics and stability. By way of example, said at least one physiologically acceptable excipient may be selected among antioxidants, chelating agents, preservatives, antimicrobial agents, polymers provided with bioadhesive properties, viscosity increasing agents, solvents and the like.

The pharmaceutical composition in form of emulsion or microemulsion of the invention herein disclosed may be packaged in primary packaging configurations well known in the art. Suitable primary packaging types can be selected in the groups comprising, but not limited to: ampoules, vials, bottles, pre-filled syringes and the like. In an embodiment, the pharmaceutical composition in form of emulsion or microemulsion of the invention herein disclosed is packaged in 5 mL or 10 mL pre-filled syringes. In a preferred embodiment, the pharmaceutical composition in form of emulsion or microemulsion of the invention herein disclosed is packaged in 10 mL, 20 mL or 50 mL vials. In another preferred embodiment, the pharmaceutical composition in form of emulsion or microemulsion of the invention herein disclosed is packaged in 10 mL, 20 mL or 50 mL ampoules. The pharmaceutical composition in form of emulsion or microemulsion of the invention herein disclosed is administered by means of endoscopic injection needles. Preferably, the composition is manually administered at room temperature.

Another aspect of the invention herein disclosed provides a kit for use in an endoscopic procedure, said kit comprising:
  a) pharmaceutical composition in form of emulsion or microemulsion according to the invention herein disclosed;
  b) an endoscopic injection needle;
  c) instruction for use.

In the preparation of said kit, said pharmaceutical composition in form of emulsion or microemulsion according to the invention herein disclosed may be packaged in primary packaging configurations well known in the art. Suitable primary packaging types can be selected in the groups comprising, but not limited to: ampoules, vials, bottles, pre-filled syringes and the like. In an embodiment, in the preparation of said kit, the pharmaceutical composition in form of emulsion or microemulsion of the invention herein disclosed is packaged in 5 mL or 10 mL pre-filled syringes. In a preferred embodiment, in the preparation of said kit, the pharmaceutical composition in form of emulsion or microemulsion of the invention herein disclosed is packaged in 10 mL, 20 mL or 50 mL vials. In another preferred embodiment, in the preparation of said kit, the pharmaceutical composition in form of emulsion or microemulsion of the invention herein disclosed is packaged in 10 mL, 20 mL or 50 mL ampoules. In the preparation of said kit according to the invention herein disclosed, suitable endoscopic injection needles may have a diameter of the needle ranging from 12 gauge to 35 gauge, preferably from 15 gauge to 30 gauge, more preferably from 17 gauge to 28 gauge. In the preparation of said kit according to the invention herein disclosed, suitable endoscopic injection needles may have a length ranging from 100 cm to 300 cm, preferably from 120 cm to 260 cm, more preferably from 140 cm to 250 cm. In the preparation of said kit according to the invention herein disclosed, suitable endoscopic injection needles may have an outer diameter ranging from 1.0 mm to 4.0 mm, preferably from 1.5 mm to 3.0 mm, more preferably from 1.8 mm to 2.5 mm. In the preparation of said kit according to the invention herein disclosed, suitable endoscopic injection needles may be composed of materials selected in the groups comprising, but not limited to: polymers or copolymers, such as polyethylene (PE), polypropylene (PP), polyvinylchloride (PVC), polycarbonate (PC), polytetrafluoroethylene (PTFE), polyethylene terephthalate (PET), polystyrene (PS), polyamide (PA), epoxy resins, polyurethane, polyester, polymethyl methacrylate and the like; rubbers, such as silicone rubber, natural rubber and the like; metals and metal alloys such as aluminium, titanium, iron, chromium, nickel, molybdenum, stainless steel, and the like. Any combination of the above materials may be used to form the appropriate endoscopic injection needle. Endoscopic injection needles suitable for the preparation of the kit according to the invention herein disclosed can be found easily on the market; by way of example, a suitable injection needle can be selected from the marketed injection needles comprising, in a non-limiting way Cook® AcuJect® Variable Injection Needles, Cook® Injectaflow® Variable Injection Needles, Boston Scientific® Interject® Injection Therapy Needles Catheters, G-Flex® Injection Needles, Endo-Flex® Sclerotherapy Needles, ConMed™ Click-Tip™ Injection Needles, Medi-Globe® Injectra® Injection Needle, Olympus® InjectorForce Max™, US Endoscopy™ Articulator™ injection needle, US Endoscopy™ Vari-Safe™ injection needle, Kimberly-Clarck™ injection needle catheters, and the like.

In a preferred application of the invention, the pharmaceutical composition in form of emulsion or microemulsion according to the invention herein disclosed is used in an endoscopic resection procedure by sucking a volume of emulsion from its primary container by means of a syringe, injecting a suitable volume of said emulsion by means of an endoscopic injection needle inserted in the working channel of the endoscope immediately under the superficial mucosal layer, to depose a liquid volume into the submucosal layer that becomes a cushion when in place: the elevation of the mucosal surface allow the endoscopist to perform an easy resection of the mucosal lesion found during the execution of the endoscopic procedure even if the lesion is flat and thus not protruding into the intestinal or esophageal or gastric lumen According to a preferred embodiment of the invention herein disclosed, the pharmaceutical composition in form of emulsion or microemulsion is in liquid phase both at room temperature (i.e. about 20-25° C.) and at body temperature (i.e. about 37° C.). According to another preferred embodiment, said composition has a viscosity below about 150 cP (centipoises), more preferably below about 100 cP (centipoises), much more preferably below about 50 cP (centipoises). According to another preferred embodiment, said composition has a viscosity below about 20 cP (centipoises), preferably below about 10 cP (centipoises).

According to the invention, said viscosity is measured at about 25° C., at about 30° C. and/or at about 37° C., preferably using a Brookfield LVDV-III Ultra Programmable Rheometer™ equipped with a Brookfield Small Sample Adapter™ device and using Brookfield™ spindle N. 31. Alternatively, said viscosity is measured using a Brookfield LVDV-III Ultra Programmable Rheometer™ equipped with a Brookfield Enhanced UL Adapter™ device and using Brookfield™ spindle N. 00.

In a preferred embodiment, the viscosity of said pharmaceutical composition in form of emulsion or microemulsion, measured at 25° C., is below 150 cP, preferably below 100 cP, more preferably below 50 cP. In a preferred embodiment, the viscosity of said pharmaceutical composition in form of emulsion or microemulsion, measured at 30° C., is below 150 cP, preferably below 100 cP, more preferably below 50 cP. In a preferred embodiment, the viscosity of said pharmaceutical composition in form of emulsion or microemulsion, measured at 37° C., is below 150 cP, preferably below 100 cP, more preferably below 50 cP. In a more preferred embodiment, the viscosity of said pharmaceutical composition in form of emulsion or microemulsion, measured at 25° C., at 30° C. and/or at 37° C. is below 20 cP, preferably below 10 cP.

The presence of at least one dye into the cushion helps the endoscopist to visualize the structures beneath the mucosa (e.g. the submucosal layer and the external muscular wall), thereby lowering the risk that the endoscopist, performing the resection procedure, may cause damages to said structures: as a matter of facts, the dye make him able to distinguish between the cushion cavity and the mucosal basement. The removal of the lesion from the mucosal surface generates a hole into the basement that has to be healed and the presence, into the pharmaceutical compositions according to the invention herein disclosed, of an agent characterized by trophic activity on the epithelial cells of the gastrointestinal mucosa has the aim of accelerating the healing of the mucosal wound. The persistency of the cushion generated by the injected volume of the pharmaceutical composition in form of emulsion or microemulsion according to the invention herein disclosed is long-lasting enough to allow the endoscopic resection procedure to be performed without the need to re-inject said composition every couple of minutes, as it generally happens when normal saline solution is used.

In view of the above, a first advantage provided by the composition in form of emulsion or microemulsion of the invention is to ensure the manually administration at room temperature (20-25° C.) without the need of cooling the composition and/or the endoscopic injection needle.

A second advantage of the composition of the invention is to avoid any risk to have unwanted gelation into the endoscopic injection needle, while the composition is administered during the endoscopic procedure.

A further advantage of the composition of the invention is the ability to provide a cushion high and/or long-lasting enough to allow a safe completion of the endoscopic resection procedure, such as polypectomy, EMR and/or ESD.

A further advantage is the possibility to add at least one dye, obtaining the improvement of the visibility of the submucosal layer to the operator with the consequent improvement of the safety and the reduction of the risk of damaging the structures beneath the mucosa.

A further advantage is the possibility to add at least one trophic agent, obtaining the improvement of the wound healing of the mucosa, with the promotion of the cellular growth and related differentiation.

DEFINITIONS

References in the specification to "one embodiment", "an embodiment" and similar indicate that the described embodiment may include a particular aspect, feature, structure or characteristic. Moreover, such phrases may, but do not necessarily, refer to the same embodiment referred to in other portions of the specification. Further, when a particular aspect, feature, structure or characteristic is described in connection with an embodiment, it is within knowledge of a person skilled in the art to affect or connect said aspect, feature, structure or characteristic with other embodiments, whether or not explicitly described.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics (and optionally physiologically acceptable excipients and/or adjuvants) of the invention are included.

The terms "consists of", "consisting of" are to be construed as a closed term.

The singular forms "a", "an" and "the" include plural references unless the context clearly dictates otherwise. Thus, for example, a reference to "a compound" includes a plurality of such compounds. It is further noted that the claims may be drafted to exclude any optional element. As such, this statement is intended to serve as antecedent basis for the use of exclusive terminology, such as "solely", "only", and the like, in connection with the recitation of claims elements or use of a "negative" limitation.

The term "and/or" means anyone of the items, any combination of the items, or all the items with which this term is associated.

Unless indicated otherwise herein, the term "about" is intended to include values, e.g. weight percentages, proximate to the recited range that are equivalent in terms of the functionality of the individual ingredient, the composition, or the embodiment.

A person skilled in the art will recognize that, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range.

A person skilled in the art will recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of anyone or more of members of a recited group. Accordingly, provisos may apply to any of the disclosed categories or embodiments whereby anyone or more of the recited elements, species, or embodiments, may be excluded from such categories or embodiments, for example, as used in an explicit negative limitation.

As well known in the art, the term "Emulsion" refers to a heterogeneous preparation composed of two immiscible liquids (by convention described as oil and water), one of which is dispersed as fine droplets uniformly throughout the other. The phase present as small droplets is called the disperse, dispersed, or internal phase and the supporting liquid is known as the continuous or external phase. Emulsions are conveniently classified as oil-in-water (o/w) or water-in-oil (w/o), depending on whether the continuous phase is aqueous or oily.

"Microemulsions" are thermodynamically stable, transparent (or translucent) dispersions of oil and water that are stabilized by an interfacial film of surfactant molecules. The surfactant may be pure, a mixture, or combined with a co-surfactant such as a medium-chain alcohol. Microemulsions are readily distinguished from normal emulsions by their transparency, their low viscosity, and more fundamentally their thermodynamic stability and ability to form spontaneously. The dividing line, however, between the size of a swollen micelle (~10-140 nm) and a fine emulsion droplet (~100-600 nm) is not well defined, although microemulsions are very labile systems and a microemulsion droplet may disappear within a fraction of a second whilst another droplet forms spontaneously elsewhere in the system. The above definitions of "emulsion" and "microemulsion" were taken from Gillian M. Eccleston "Emulsion and Microemulsion" Encyclopedia of Pharmaceutical Technology, 2007, 3$^{rd}$ edition, Informa Healthcare.

The term "endoscopic mucosal resection" (EMR) refers to an endoscopic technique developed for removal of sessile or flat neoplasms confined to the superficial layers (mucosa and submucosa) of the GI tract.

The term "endoscopic mucosal dissection" (ESD) refers to an endoscopic technique developed specifically for removing larger lesions.

"Endoscopic injection needles", known also under the names of "injection needles" or "injection needle catheters" or "endoscopic injection needle catheters", are devices which can be long up to about 230 cm and which include a relatively long catheter within which an inner injection tube having a distal injection needle is slideably disposed. Generally, a proximal actuating handle is coupled to the catheter and the injection tube for moving one relative to the other when necessary. The needle is generally retractable. Fluid access to the injection tube is typically provided via a luer connector on the handle. Endoscopic injection needle devices are typically delivered to the injection site through the working channel of the endoscope. In order to protect the lumen of the endoscope working channel from damage, the handle of the infusion needle device is manipulated to withdraw the distal injection needle into the lumen of the catheter before inserting the device into the endoscope. This is important to prevent exposure of the sharp point of the injection needle as the device is moved through the lumen of the endoscope. When the distal end of the endoscopic injection needle device is located at the injection site, its handle is again manipulated to move the injection needle distally out of the lumen of the catheter. When advanced to the most distal position, the exposed portion of the injection needle is approximately 4-6 mm in length.

"In (or under) laboratory test conditions" or "in laboratory conditions" or "in laboratory tests", as used herein, refer to in-vitro conditions, such as methods, equipment and instruments commonly used in laboratory tests to perform a physical-chemical characterisation of a composition. The term refers to methods, equipment and instruments used and performed in laboratory. By way of example, the viscosity test or the test of the climatic chamber, described in the Examples 6 and 7 reported hereinafter and used to verify whether a composition is in liquid phase or in gel phase, are tests performed in laboratory, thus they are performed in "laboratory test conditions".

"Up to 40° C." or "temperature up to 40° C." refer to any temperature comprised between 5° C. and 40° C., preferably about 5° C., about 20° C., about 25° C. about 30° C. and/or 37° C.

"Body temperature" refers to the level of heat produced and sustained by the body processes. Heat is generated within the body through metabolism of nutrients and lost from the body surface through radiation, convection, and evaporation of perspiration. Heat production and loss are regulated and controlled in the hypothalamus and brainstem. Normal adult body temperature, as measured orally, is 37° C., even though little variations are normally recorded throughout the day.

"Room temperature" (RT) is generally defined as the ambient air temperature in whatever environment being used for a given procedure. More specifically, it is defined as 20-25° C., as some ambient temperatures, by nature, do not fall within this range. Generally, protocols calling for steps to be performed at RT require that temperatures do not fall below 18° C., and do not exceed 27° C.

"Critical Gelation Concentration" (CGC), for a composition containing an inverse thermosensitive polymer represents the concentration of said polymer above which said composition is able to transition from a liquid phase to a gel phase in response to the raise in temperature.

"Critical Gelation Temperature" (CGT) represents the temperature above which a composition containing an inverse thermosensitive polymer at a concentration equal to or above the critical gelation concentration transitions from a liquid phase to a gel phase.

"Lugol's solution": is a solution of elemental iodine and potassium iodide in water.

The "viscosity" defines the resistance of a liquid or semisolid against flow. The flow of liquids or semisolids is described by viscosity, or, more precisely, by shear viscosity q. The shear viscosity of a fluid expresses its resistance to shearing flows, where adjacent layers move parallel to each other with different speeds. Common units of measurement of viscosity are the pascal-second (Pa·s), the poise (P) and "cP" centipoises. 1 poise (P) corresponds to 0.1 pascal-second (Pa·s); 1 centipoise (cP) corresponds to 1 millipascal-second (mPa·s).

"Percentage by weight with respect to the weight of the composition (w/w)" and "Percentage by weight with respect to the volume of the composition (w/v)": define the percentage amount of a component or substance in the composition. Considering that the density of the composition in form of emulsion or microemulsion is equivalent to the density of the water (1.0 g/mL), the percentage by weight with respect to the weight of the composition (w/w) is considered equivalent to percentage by weight with respect to the volume of the composition (w/v). For the purpose of the present invention, the two definitions are therefore interchangeable.

PEG: polyethylene glycol.

The following examples are included for purpose of illustration of certain aspects and embodiments of the invention, and are not intended to limit the invention.

EXAMPLES

Example 1—Emulsion

| Component | g/100 g |
| --- | --- |
| Methylene blue | 0.0010 |
| Sodium chloride | 0.9000 |
| Poloxamer 188 | 10.0000 |
| Soybean oil | 0.1600 |
| Glycerol | 0.0050 |
| Egg lecithin | 0.0240 |
| Sodium oleate | 0.0006 |
| Water for injection | q.s. 100.0 g |

The manufacture of the composition is described hereinafter (for 10.00 Kg of final composition):

a) In a suitable vessel provided with a stirrer, 8600 mL of water for injection are loaded; then, 90.00 g of sodium chloride are added. The mixture is kept under stirring until a complete dissolution is achieved. The obtained solution is cooled at a temperature ranging between 5° C. and 10° C.; then, 1000.00 g of poloxamer 188 are added under stirring. The mixture is kept under stirring until a complete dissolution is achieved.

b) In a suitable vessel provided with a stirrer, about 181 mL of water for injection are loaded; the temperature is raised at 80° C. 2.40 g of egg lecithin, 0.50 g of glycerol and 0.06 g of sodium oleate are added under stirring. The stirrer is operated until complete homogenization; then, 16.00 g of soybean oil are added. The mixture is kept at T=80° C. under stirring until an homogeneous emulsion is obtained. The emulsion is then cooled at a temperature below 30° C.

c) The emulsion obtained in step b) is added to the mixture obtained in step a) under stirring. Then, 0.10 g of methylene blue are added under stirring. The mixture is kept under stirring until homogeneity.

d) The pH of the mixture of step c) is measured and it is brought, if necessary, within the range 5.0-7.0.

e) The mixture is brought to a final weight of 10.00 Kg by adding water for injection.

f) The final composition is filtered through a 0.45 μm filter and is packed in 20 mL vials capped with rubber caps and aluminum rings. The vials are sterilized at 121° C. for 20 minutes.

Example 2—Emulsion

| Component | g/100 g |
| --- | --- |
| Methylene blue | 0.0010 |
| Sodium chloride | 0.9000 |
| Poloxamer 407 | 9.0000 |
| Soybean oil | 0.1600 |
| Glycerol | 0.0050 |
| Egg lecithin | 0.0240 |
| Sodium oleate | 0.0006 |
| Water for injection | q.s. 100.0 g |

The composition was obtained by a process similar to that described in Example 1.

Example 3—Emulsion

| Component | g/100 g |
| --- | --- |
| Methylene blue | 0.0010 |
| Sodium chloride | 0.9000 |
| Poloxamer 188 | 10.0000 |
| Soybean oil | 0.0800 |
| Glycerol | 0.0025 |
| Egg lecithin | 0.0120 |
| Sodium oleate | 0.0003 |
| Water for injection | q.s. 100.0 g |

The composition was obtained by a process similar to that described in Example 1.

Example 4—Emulsion

| Component | g/100 g |
| --- | --- |
| Methylene blue | 0.0010 |
| Sodium chloride | 0.9000 |
| Poloxamer 407 | 9.0000 |
| Soybean oil | 0.0800 |
| Glycerol | 0.0025 |
| Egg lecithin | 0.0120 |
| Sodium oleate | 0.0003 |
| Water for injection | q.s. 100.0 g |

The composition was obtained by a process similar to that described in Example 1.

Example 5—Emulsion

| Component | g/100 g |
|---|---|
| Methylene blue | 0.0010 g |
| Sodium chloride | 0.9000 g |
| L-Glutamic acid | 1.0000 g |
| Poloxamer 188 | 10.000 g |
| Soybean oil | 0.1600 g |
| Glycerol | 0.0050 g |
| Egg lecithin | 0.0240 g |
| Sodium oleate | 0.0006 g |
| Sodium hydroxide | q.s. to bring the pH within 5.0 and 7.0 |
| Water for injection | q.s. to 100.0 g |

The manufacture of the composition is described hereinafter (for 10.00 Kg of final composition):

a) In a suitable vessel provided with a stirrer, 8600 mL of water for injection are loaded; then, 90.00 g of sodium chloride are added. The mixture is kept under stirring until a complete dissolution is achieved. The obtained solution is cooled at a temperature ranging between 5° C. and 10° C.; then, 1000.00 g of poloxamer 188 are added under stirring. The mixture is kept under stirring until a complete dissolution is achieved.

b) In a suitable vessel provided with a stirrer, about 181 mL of water for injection are loaded; the temperature is raised at 80° C. 2.40 g of egg lecithin, 0.50 g of glycerol and 0.06 g of sodium oleate are added under stirring. The stirrer is operated until a complete homogenization; then, 16.00 g of soybean oil are added. The mixture is kept at T=80° C. under stirring until an homogeneous emulsion is obtained. The emulsion is then cooled at a temperature below 30° C.

c) The emulsion obtained in step b) is added to the mixture obtained in step a) under stirring. Then, 0.10 g of methylene blue and 100.00 g of L-glutamic acid are added under stirring. The mixture is kept under stirring until homogeneity.

d) The pH of the mixture of step c) is measured and it is brought within the range 5.0-7.0 by adding 10% NaOH in water for injection.

e) The mixture is brought to a final weight of 10.00 Kg by adding water for injection.

f) The final composition is filtered through a 0.45 µm filter and is packed in 20 mL vials capped with rubber caps and aluminum rings. The vials are sterilized at 121° C. for 20 minutes.

Example 6—Viscosity Measurement in Laboratory Test

The viscosities of the pharmaceutical compositions according to Examples 1 to 4 were measured in laboratory conditions at three different temperatures: T=25° C., T=30° C. and T=37° C. The measurements were performed using a Brookfield LVDV-III Ultra Programmable Rheometer™ equipped with a Brookfield Small Sample Adapter™ device. The Brookfield Small Sample Adapter™ comprised a sample chamber which fitted into a water jacket so that precise temperature control was achieved by means of a circulating thermostating water bath. For the measurements, two different spindles were used, depending upon the viscosity value: for low viscosity values (registered at T=25° C., 30° C. and 37° C. for compositions according to example 1 to 4 and at T=25° C. and 30° C. for the reference), Brookfield™ spindle N. 31 was used; for high viscosity values (registered at T=37° C. for the reference), Brookfield™ spindle N. 25 was used.

A solution of poloxamer 407 in normal saline was used as reference. The reference was prepared dissolving poloxamer 407 in normal saline to obtain a final concentration of poloxamer 407 equal to its critical gelation concentration (about 15% by weight with respect to the total weight of the solution). The composition of the reference solution is hereinafter reported:

| Component | g/100 g |
|---|---|
| Sodium chloride | 0.9000 |
| Poloxamer 407 | 15.0000 |
| Water for injection | q.s. 100.0 g |

The viscosities of the compositions according to Examples 1 to 4 are reported in the table below with respect to the reference solution:

| | Viscosity (cP) | | |
|---|---|---|---|
| Composition | Viscosity at 25° C. | Viscosity at 30° C. | Viscosity at 37° C. |
| Reference (solution) | 60 | 88 | 1044 |
| Composition of Example 1 | 5.70 | 5.45 | 4.95 |
| Composition of Example 2 | 6.45 | 6.80 | 6.30 |
| Composition of Example 3 | 5.70 | 5.60 | 5.00 |
| Composition of Example 4 | 6.70 | 6.75 | 6.25 |

The reference solution showed a gel-forming ability upon heating from 25° C. to body temperature (i.e. 37° C.) in laboratory conditions, passing from a liquid state having a viscosity of about 60 cP to a gel state, having a viscosity of 1044 cP. The pharmaceutical compositions according to Examples 1 to 4 did not show any gel-forming ability, since their viscosities remained quite constant upon heating from 25° C. to body temperature (i.e. 37° C.).

Example 7—Phase Characterization by Means of a Climatic Chamber Test

In order to characterize whether a composition in form of emulsion or microemulsion of the invention is in liquid phase or in gel phase, a climatic chamber test was performed in addition to the viscosity test described in Example 6. The pharmaceutical compositions according to Examples 1 to 4 and the reference solution described in Example 6 (poloxamer 407 15% in normal saline) were packed_in sealed vials, which were then placed into a climatic chamber thermostated at 40° C. After two hours, the phase (liquid or gel) of said compositions was easily checked turning upside down the vials: in the case of the compositions according to Examples 1 to 4, there was a flow of liquid while the vial was being turned upside down; on the contrary, in the case of the reference solution (poloxamer 407 15% in normal saline), there was no flow of liquid into the vial, and the composition in gel phase remained atop the vial.

Figure 2:
FIG. 2: The second cushion generated by the second injection of the composition according to Example 1 into the sub-mucosal layer of an ex-vivo porcine stomach.
Figure 3:
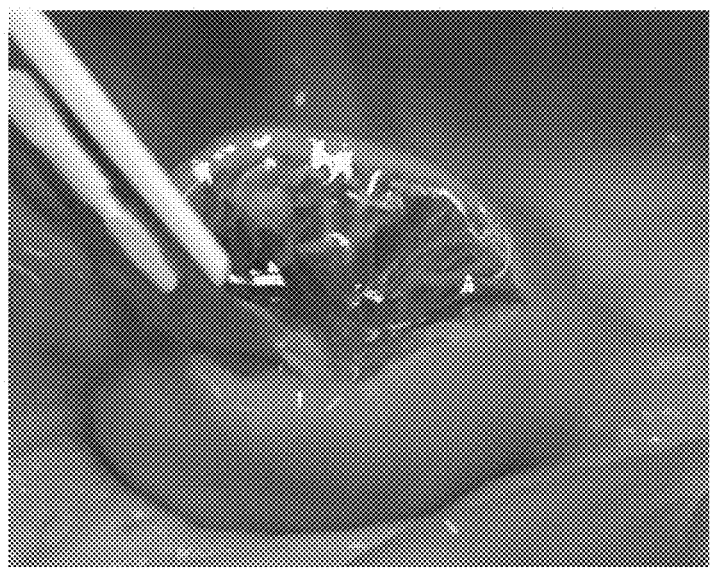
FIG. 3: The first cushion of FIG. 1 after cut immediately after the injection, a viscous product with a good consistency is visible into the sub-mucosal layer.
Figure 4:
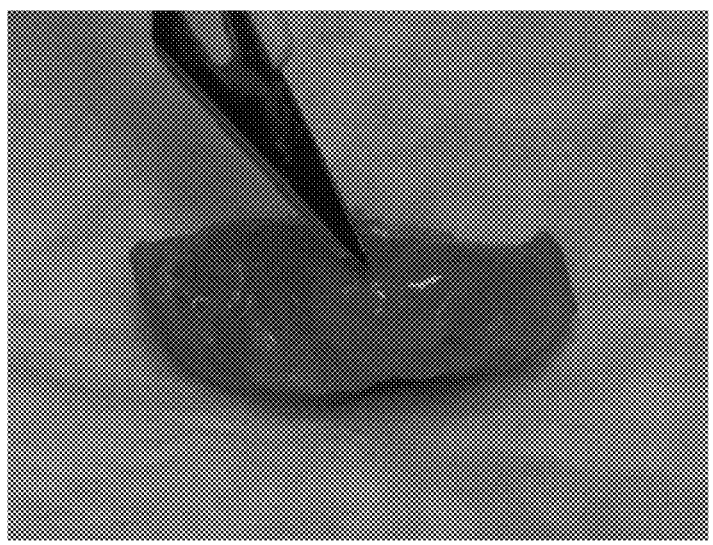
FIG. 4: A specimen of the mucosa of the first cushion of FIG. 1 after resection, wherein is visible that the product formed by the composition injected remains attached to the excised piece.
Figure 5:
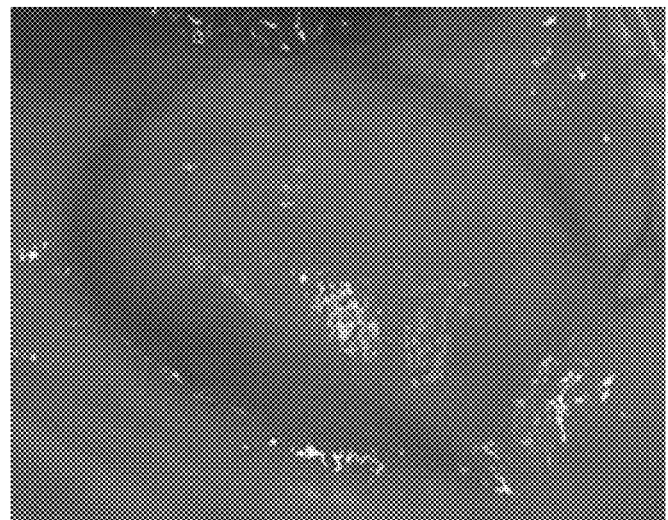
FIG. 5: The second cushion of FIG. 2 after 15 minutes from injection.
Figure 6:
FIG. 6: The second cushion of FIG. 2 after cut, a viscous product with a good consistency similar to that of FIG. 3 is visible into the sub-mucosal layer.
Figure 7:
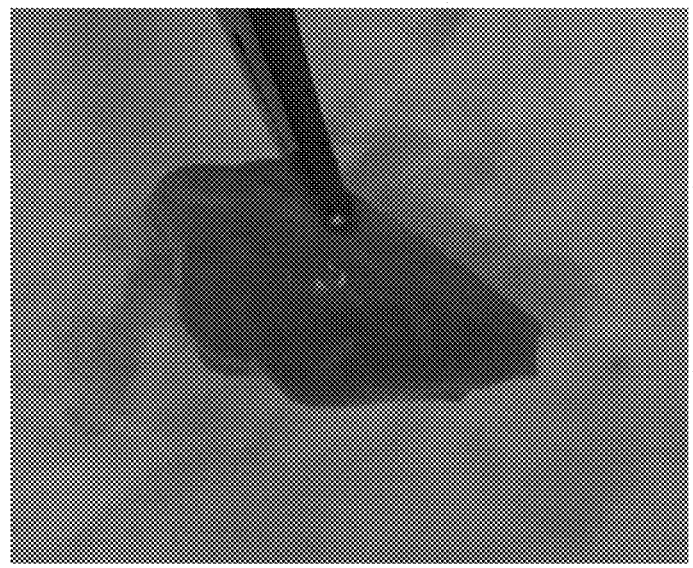
FIG. 7: A specimen of the mucosa of the second cushion of FIG. 2 after resection, wherein is visible that the product formed by the composition injected remains attached to the excised piece.

Example 8—Injection of the Composition According to Example 1 into the Submucosal Layer of an Ex Vivo Porcine Stomach An ex vivo porcine stomach was placed into a water-bath maintained at 37.0° C.±0.5° C. by means of a calibrated thermostat. Once the stomach reached the desired temperature (37° C.±0.5° C.), it was then placed on an examination couch. The composition according to Example 1 was injected into the submucosal layer of the stomach by means of an endoscopic injection needle; the injected volume was 5.0 mL+0.5 mL, in order to create a visually adequate submucosal elevation. Two injections were performed; in both cases, the generated submucosal cushions (FIGS. 1 and 2) were able to elevate the mucosal wall in a way suitable to allow a typical resection of polyps by means of a snare or of an electroscalpel, in accordance to typical endoscopic resection procedures such as EMR and ESD. One of the cushions was cut by means of a scalpel immediately after the injection; after the cut, the composition seemed to have provided a viscous product into the submucosal layer which had a good consistency (FIG. 3). A specimen of the mucosa was resected and visually examined: the product formed by the composition according to Example 1 remained attached to the piece excised (FIG. 4). The other cushion was held in place for 15 minutes from the injection before cutting. During this time, the cushion did not show any change in shape and in height (FIG. 5). After 15 minutes, the second cushion was cut in a way similar to the first cushion (FIG. 6). The visual examination of the specimen after cutting revealed the presence of a viscous product into the submucosal layer which had a consistency similar to that obtained in the first cushion (FIG. 7). The test revealed that the composition according Example 1, which was not able to transition from a liquid phase to a gel phase upon heating from 25° C. to body temperature (i.e. 37° C.) in laboratory test conditions (as reported in Examples 6 and 7), was contrarily able to generate a high, long-lasting submucosal cushion once injected into the submucosal layer of a porcine stomach. The cutting of such a cushion revealed that the composition according to Example 1 had surprisingly formed a viscous product into the submucosal layer; after the removal of a specimen of mucosa from the cushion, such a product remained attached to said specimen for 10 minutes.

Example 9—Microemulsion

| Component | g/100 ml |
| --- | --- |
| Methylene blue | 0.0010 |
| Sodium chloride | 0.5000 |
| Poloxamer 188 | 10.0000 |
| Soybean oil | 0.0050 |
| PEG-15 hydroxystearate | 0.1000 |
| Water for injection | q.s. to 100.0 ml |

The manufacture of the composition is described hereinafter.

a) In a suitable vessel provided with a stirrer, the lipophilic compound and the non-ionic surfactant are loaded and mixed; then a suitable amount of warm water for injection is poured into the oily phase under stirring. The mixture is maintained stirred and warmed until a micro-emulsion is obtained.

b) In a second tank, the remaining amount of water for injection is warmed; then the micro-emulsion prepared at step a) is poured drop wise under stirring.

c) The polymer is added to the micro-emulsion of step b), and the mixture is maintained under stirring until complete dissolution is achieved.

d) Sodium chloride is added under stirring until complete dissolution is achieved.

e) The dye is added under vigorous stirring until complete dissolution is achieved.

f) The pH of the mixture of step e) is measured (specification: 5.0-7.5).

g) The mixture is brought to final volume by adding water for injection.

h) The final composition is sterilized by sterilizing filtration thanks to the very small droplets size (below 100 nm) of the micro-emulsion; thus it is filtered through a 0.22 μm filter and is packed by aseptic processing in vials capped with rubber caps and aluminium rings.

Example 10—Microemulsion

| Component | g/100 ml |
| --- | --- |
| Methylene blue | 0.0010 |
| Sodium chloride | 0.5000 |
| Poloxamer 188 | 10.0000 |
| Medium chain triglycerides | 0.0200 |
| PEG-15 hydroxystearate | 0.0800 |
| Water for injection | q.s. 100.0 ml |

The composition was obtained by a process similar to that described in Example 9.

Example 11—Microemulsion

| Component | g/100 ml |
| --- | --- |
| Methylene blue | 0.0010 |
| Sodium chloride | 0.5000 |
| Poloxamer 188 | 10.0000 |
| Soybean oil | 0.2000 |
| Polyoxyl-35 castor oil | 3.0000 |
| Water for injection | q.s. to 100.0 ml |

The composition was obtained by a process similar to that described in Example 9.

Example 12—Microemulsion

| Component | % w/v |
| --- | --- |
| Methylene Blue | 0.001 |
| Sodium Chloride | 0.440 |
| Poloxamer 188 | 10.000 |
| Polyoxyl-15 Hydroxystearate | 0.500 |
| Medium chain triglycerides | 0.100 |
| WFI | q.s. to 100 ml |

The composition was obtained by a process similar to that described in Example 9.

Example 13—Microemulsion

| Component | g/100 ml |
| --- | --- |
| Methylene blue | 0.0010 |
| Sodium chloride | 0.5000 |
| Poloxamer 188 | 10.0000 |

-continued

| Component | g/100 ml |
| --- | --- |
| Medium chain triglycerides | 1.0000 |
| PEG-15 hydroxystearate | 4.0000 |
| Water for injection | q.s. to 100 ml |

The composition was obtained by a process similar to that described in Example 9.

Example 14—Microemulsion

| Component | g/100 ml |
| --- | --- |
| Indigo carmine | 0.001 |
| Sodium chloride | 0.500 |
| Poloxamer 188 | 10.000 |
| Polyoxyl-15 Hydroxystearate | 0.600 |
| Medium chain triglycerides | 0.100 |
| Water for injection | q.s. to 100 ml |

The composition was obtained by a process similar to that described in Example 9.

Example 15—Microemulsion

| Component | g/100 ml |
| --- | --- |
| Methylene Blue | 0.001 |
| Sodium chloride | 0.500 |
| Poloxamer 188 | 10.000 |
| Polyoxyl-15 Hydroxystearate | 0.500 |
| Medium chain triglycerides | 0.100 |
| Water for injection | q.s. to 100 ml |

The composition was obtained by a process similar to that described in Example 9.

Example 16—Microemulsion

| Component | g/100 ml |
| --- | --- |
| Sodium chloride | 0.500 |
| Poloxamer 188 | 10.000 |
| Polyoxyl-35-castor oil | 3.000 |
| Soybean oil | 0.200 |
| Water for injection | q.s. to 100 ml |

The composition was obtained by a process similar to that described in Example 9, without the step e).

Example 17—Characterisation of the Micro-Emulsion Droplet Size by Dynamic Light Scattering (DLS)

The oil-in-water micro-emulsions of the present invention are thermodynamically stable, can be prepared spontaneously, and are transparent.

The dynamic light scattering (DLS) technique was used to characterize the micro-emulsion droplet size.

INSTRUMENT: Zetasizer Nano® ZSP from Malvern Instruments
SAMPLE PREPARATION: None, sample not diluted
SETTING UP MEASUREMENT:
Measurement type: size
Sample:
  Material: No setting (The material optical properties are not needed for intensity-based distribution)
  Dispersant: water with bulk viscosity at 25° C.
  General options: use dispersant viscosity as sample viscosity
  Temperature: 25° C. with 60 sec of equilibration time
  Cell: disposable cuvettes DTS0012
MEASUREMENT:
  Measurement angle: 173° backscatter (NIBS default)
  Measurement duration: Automatic
  Number of measurement: at least 3
  Instructions: no one
Advanced:
  Extend duration for large particles: No
  Positioning method: Seek for optimum position
  Automatic Attenuation Selection: Yes Hereinafter the DLS analyses of the micro-emulsion of Example 15 are shown.

Two samples were withdrawn at the end of step a) and d), and were then analyzed using the instrument parameters reported above.

Figure 8:
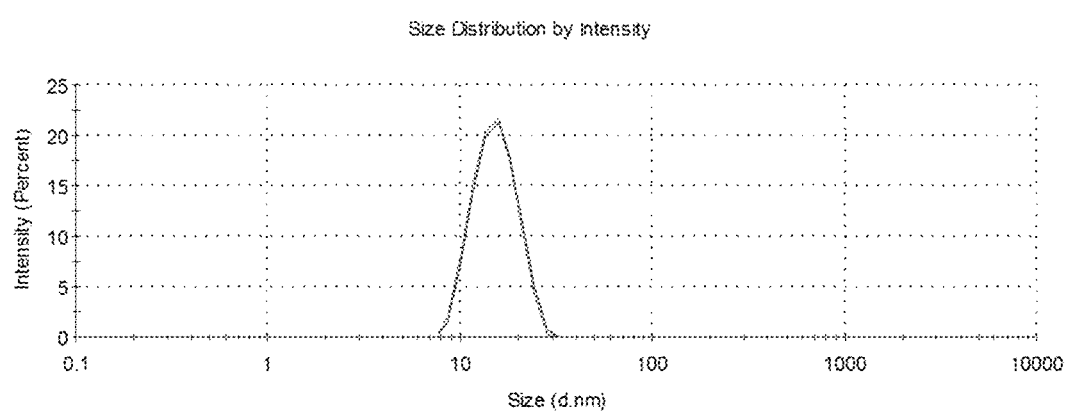
FIG. 8: The graph showing the microemulsion droplet size distribution by intensity, measured on the composition of Example 15 after step a) of the manufacturing process (see also example 9 and the Table A of Example 17).

In the following table A the results of DLS analysis on sample from step a) are reported. The relevant graph is shown in FIG. 8.

TABLE A

|  | | | Size (d · nm): | % Intensity: | St. Dev. (d · nm) |
| --- | --- | --- | --- | --- | --- |
| Z-Average (d · nm) | 14.61 | Peak 1 | 15.41 | 100.0 | 3.790 |
| PdI | 0.036 | Peak 2 | 0.000 | 0.0 | 0.000 |
| Intercept | 0.949 | Peak 3 | 0.000 | 0.0 | 0.000 |

The results show the distribution of monodisperse particles with a Z-Average around 14 nm and a polydispersity index extremely low.

Figure 9:
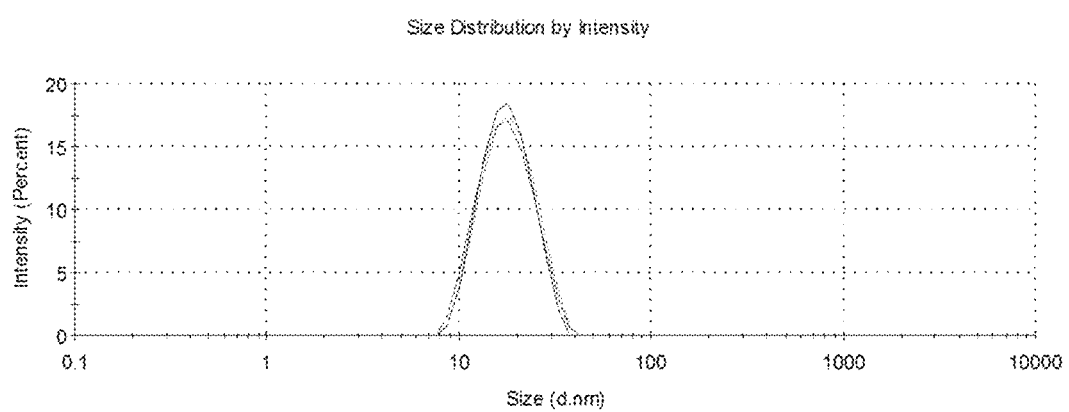
FIG. 9: The graph showing the microemulsion droplet size distribution by intensity, measured on the composition of example 15 after step d) of the manufacturing process (see also Example 9 and the Table B of Example 17).

In the following table B the results of DLS analysis on sample from step d) are reported. The relevant graph is shown in FIG. 9.

TABLE B

|  | | | Size (d · nm): | % Intensity: | St. Dev. (d · nm) |
| --- | --- | --- | --- | --- | --- |
| Z-Average (d · nm) | 14.16 | Peak 1 | 18.25 | 100.0 | 5.764 |
| PdI | 0.269 | Peak 2 | 0.000 | 0.0 | 0.000 |
| Intercept | 0.960 | Peak 3 | 0.000 | 0.0 | 0.000 |

The chart shows a unique distribution of particles with a Z-Average around 14 nm and a low polydispersity index. The measurements are reproducible with a good intercept of the correlation function (0.960).

Figure 10:
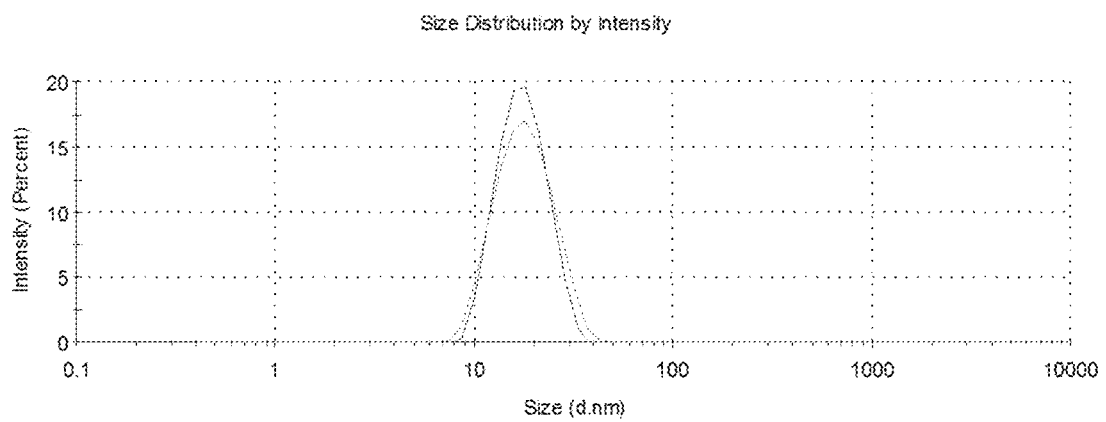
FIG. 10: Superimposing graph showing the comparison between the microemulsion droplet size distribution by intensity after step a) and after step d) of the manufacturing process, measured on the composition of example 15 (see also Example 9 and the Table C of Example 17).

In the following table C, a comparison between the results obtained at step a) and step d) is reported. The relevant graph is shown in FIG. 10.

TABLE C

| Sample | Zav (nm) | PdI |
| --- | --- | --- |
| Sample from step a) | 14.39 | 0.24 |
| Sample from step d) | 14.43 | 0.27 |

From the superposition of the particle size distributions and the two dimensional data, the two samples are equal: the small differences between them are not significant and can be attributed to experimental variability. Thus, the two samples are equal both in terms of distribution and of the Z-average.

Figure 11:
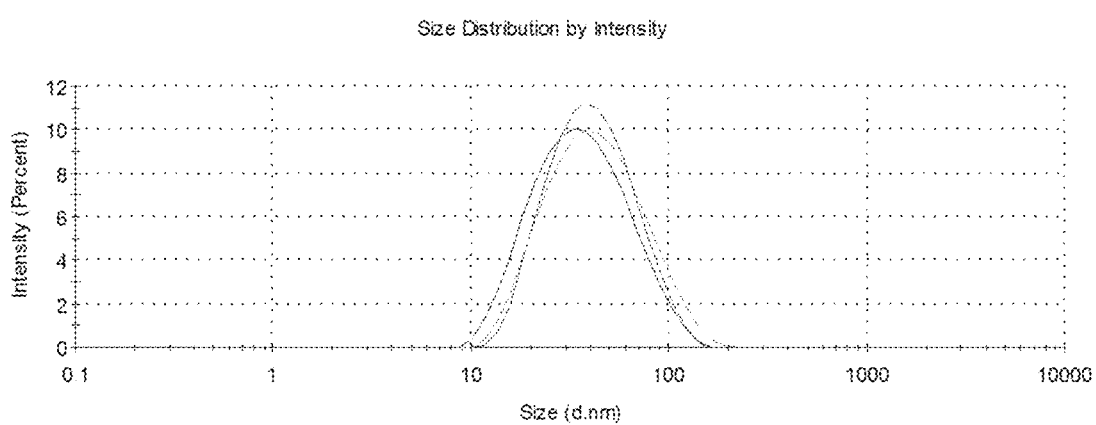
FIG. 11: The graph showing the microemulsion droplet size distribution by intensity (three replicates on the same sample), measured on the composition of Example 15 after step e) of the manufacturing process (see also Example 9 and the Table D of Example 17).

In the following table D the results of DLS analysis on sample from step e) are reported. The relevant graph is shown in FIG. 11.

TABLE D

|  |  |  | Size (d · nm): | % Intensity: | St. Dev. (d · nm) |
|---|---|---|---|---|---|
| Z-Average (d · nm) | 28.02 | Peak 1 | 44.82 | 100.0 | 22.21 |
| PdI | 0.303 | Peak 2 | 0.000 | 0.0 | 0.000 |
| Intercept | 0.147 | Peak 3 | 0.000 | 0.0 | 0.000 |

The graph shows a single distribution of particles with a Z-Average around 28 nm.

The DLS analyses of the micro-emulsion on sample from step e) of the Examples 11-13 and 14 are reported in the following table E:

TABLE E

| EXAMPLES NUMBER | Z-Average (d · nm) | PdI |
|---|---|---|
| 11 | 9.61 | 0.20 |
| 13 | 15.15 | 0.11 |
| 14 | 27.51 | 0.223 |

The DLS analyses of the micro-emulsion on sample from step a), d) of Example 12 are reported in the following table F

TABLE F

| EXAMPLES NUMBER | Z-Average (d · nm) | PdI |
|---|---|---|
| 12 after step a) | 13.98 | 0.159 |
| 12 after step d) | 16.68 | 0.305 |

Example 18—Cytotoxicity

The composition according to Example 15 was subjected to an in vitro cytotoxicity study on Mammal fibroblasts ATCC BalbC 3T3, according to ISO 10993-5.

After 24 hours of test, the following results were obtained:
The reduction of vitality of the cells in the well of the composition of Example 15 was 14.68%, and the composition was judged to be not cytotoxic.

Example 19—Cytotoxicity

The composition according to Example 10 was subjected to an in vitro cytotoxicity study on Mammal fibroblasts ATCC BalbC 3T3, according to ISO 10993-5.

After 24 hours of test, the following results were obtained:
The reduction of vitality of the cells in the well of the composition of Example 10 was 6.22%, and the composition was judged to be not cytotoxic.

Example 20—Testing on Ex Vivo Porcine Stomachs

During product development, the cushion forming ability of the different prototype formulations has been evaluated using several tests on ex vivo porcine stomachs. The porcine stomach was selected as testing system because it is a widely accepted model of the human gastrointestinal mucosa. Moreover, in scientific literature many published works on submucosal injection agents describe the use of this model for assessing the performance of the different agents in terms of height and duration of the submucosal cushion.

The efficacy of the pharmaceutical compositions according to the present invention was evaluated in the ex vivo test, in terms of height and duration of the submucosal cushion following the injection of a suitable volume.

Figure 12:
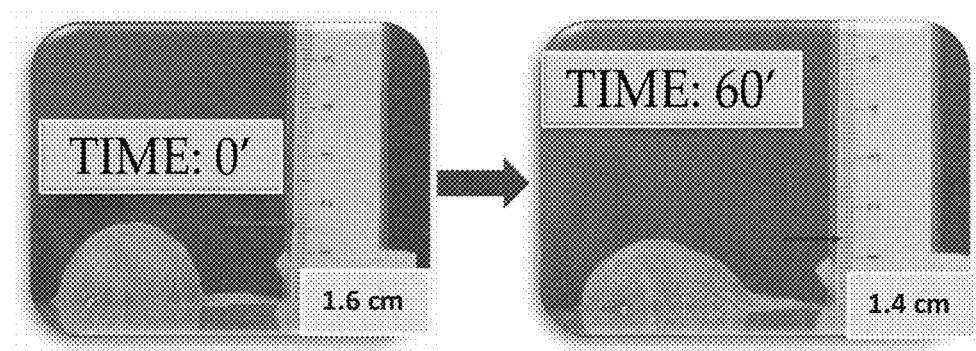
FIG. 12: Height of the sub-mucosa cushion formed upon injection of a suitable volume of the composition of Example 11, at time 0 and after 60 minutes.

A brief description of the method is reported hereinafter.
Materials
Frozen porcine stomach
Plexiglass support.
10 ml Luer-Lock Syringe
Standard Endoscopic injection needle
Method The frozen porcine stomach is thawed out and then is kept at 37° C. in a thermal blanket. The stomach is cut open using a surgical scalpel, and the internal mucosa is cleaned up using paper towels. A 10 cm×10 cm square portion is cut from the stomach and is fitted in the Plexiglas support. A suitable volume of the pharmaceutical composition is injected through the endoscopic injection needle into the submucosal layer of the resected square specimen of the porcine stomach When the submucosal cushion formation is completed, the needle is removed from the specimen. The height and time of permanence of the obtained submucosal cushion is evaluated by visual inspection. The cushion is monitored every 15 minutes up to an hour.
Results As depicted in FIG. 12, the submucosal cushion created after injection of a suitable amount of the composition of Example 11 passed from a height of 1.6 cm to 1.4 cm, thus losing only 0.2 cm over 1 hour from injection.

The results for the compositions of examples 9, 11 and 13 are reported in following table G:

TABLE G

| EXAMPLE NUMBER | HEIGHT AT T 0' | HEIGHT AT T 60' |
|---|---|---|
| 11 (see FIG. 12) | 1.6 cm | 1.4 cm |
| 9 | 1.1 cm | 1.1 cm |
| 13 | 1.2 cm | 1.1 cm |

Example 21—Preliminary Test on In Vivo Minipig

A preliminary tolerance study on a minipig was carried out on composition according to Example 5.
Purpose The purpose of the study was to investigate the tolerance of the product in minipig after gastric submucosal administration.
Methods One male Göttingen minipig, having a weight of approximately 20 kg and an age of approximately 10 months, was used for this study. The endoscopic procedure was performed with the use of an Electronic Video Endocopes Fujinon EVE200 System and Upper Gastrointestinal Electronic Video Endocopes EG-201FP. The submucosal injection agent was delivered by means of the endoscope using and endoscopic injection needle. The animal was anaesthetized prior to each endoscopic procedure. The test item was administered (about 5 ml) by endoscopic submucosal injection, using an endoscopic injection needle (Medwork® injection needle, 230 cm×2.3 mm, needle diameter 0.7 mm, Ref. N. INJ1-A1-07-5-23-230). The animal was dosed once by submucosal injection in about 55 seconds, followed by observation for 24 hours. After administration, the mucosa of the injection site and the surrounding untreated mucosa were continuously examined for 25 minutes, during which the test item caused an adequate distension with a detachment between the mucosal and submucosal layers. This detachment was still persistent 25 minutes after injection; further examinations were performed at 60 minutes and at 24 hours.

The subsequent overall observation of the injection site at about 60 minutes after the injection, showed the persistence of evident swellings.

At 24-hour observation period, gastric mucosa swellings were no longer present and gastric mucosa showed no test article related gross macroscopic changes.

Figure 13:
FIG. 13: The image shows an endoscopy in a minipig stomach (in vivo test in minipig of Example 21), and in particular the endoscopic injection needle, contained in the working channel of the endoscope, injecting the composition of Example 5 into the submucosal layer.
Figure 14:
FIG. 14: The image shows an endoscopy in a minipig stomach (in vivo test in minipig of Example 21), and in particular the submucosal cushion at the end of the administration. The interventional area has a blue contrasting colour compared to the surrounding area.
Figure 15:
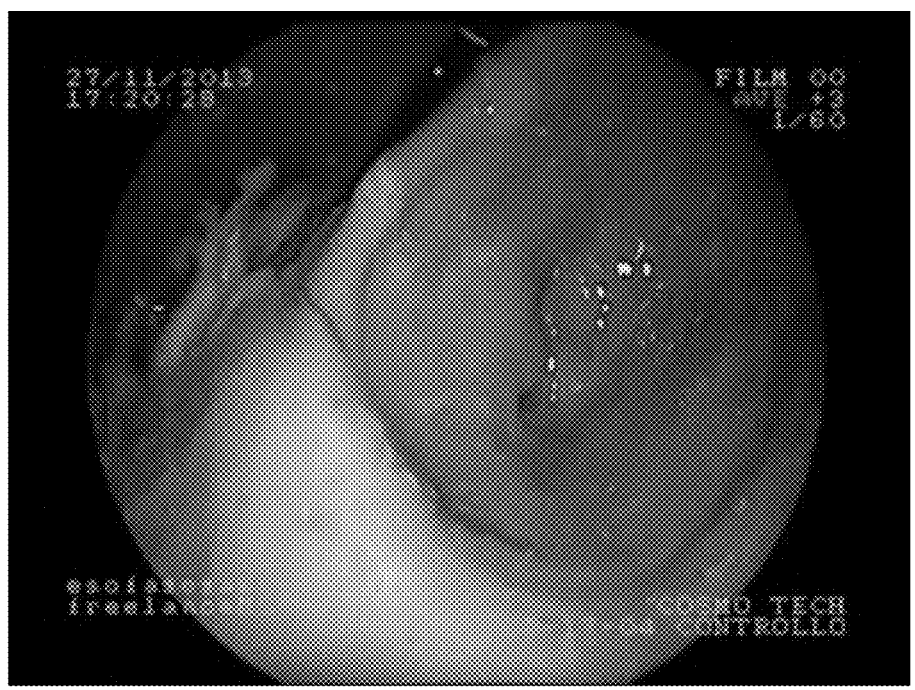
FIG. 15: The image shows an endoscopy in the minipig stomach (in vivo test in minipig of Example 21) after 24 hours from the administration of the composition of Example 5. In the area where the composition was injected, the submucosal cushion is no longer visible. The gastric mucosa showed no gross macroscopic changes due to the administration of the composition.

FIGS. 13, 14 and 15 show the administration of the test item, the submucosal cushion, and the appearance of the injection site at 24 hours post administration.

Example 22—Rheology

The viscosity variation as function of temperature was measured on the composition of example 16 by using a rotational rheometer, Kinexus pro +.

The Kinexus pro + is a rotational rheometer that applies controlled shear deformation to the sample, and it is normally used in order to evaluate and study the rheological characterization (viscosity) of compositions, as emulsions or microemulsions.

For proceeding with the measurement, the composition of example 16 was equipped with a cone plate CP60-2° at controlled shear and constant stress, 0.5 Pa; the temperature range was set between 25° C. and 50° C.

Figure 16:
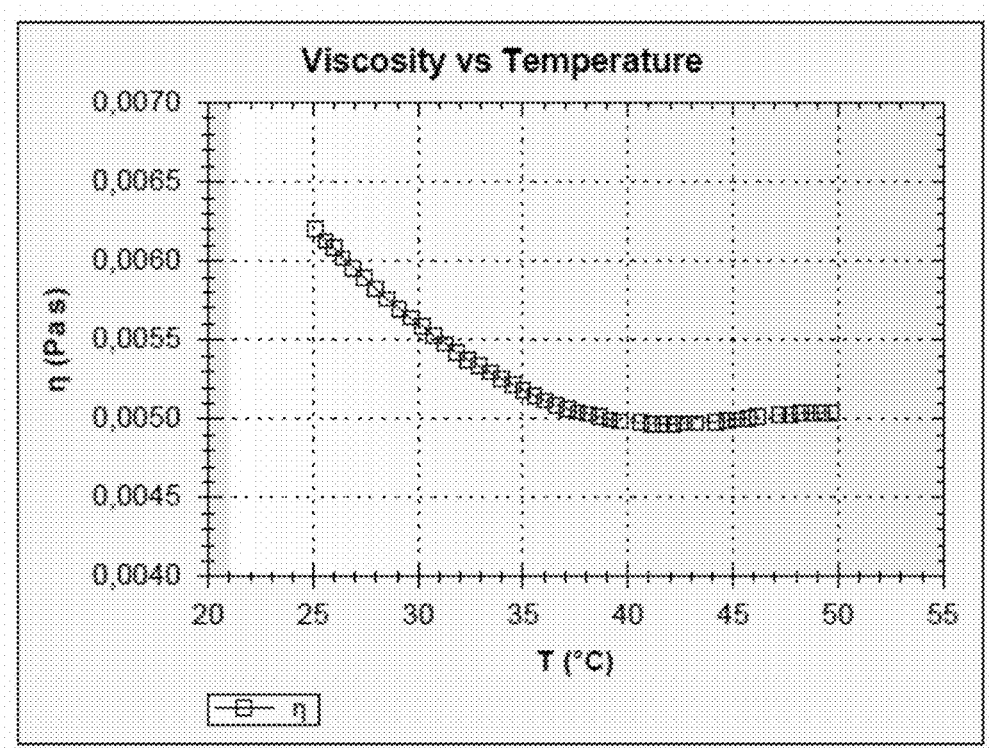
FIG. 16: The graph showing the rheogram viscosity versus temperature.

As reported in the graph of FIG. 16, the rheogram viscosity versus. temperature demonstrates that the viscosity of the composition decreases with the increasing of the temperature.

The invention claimed is:

1. A pharmaceutical composition in the form of an emulsion or a microemulsion comprising:
    (a) an aqueous phase;
    (b) an oily phase;
    (c) at least one surfactant; and
    (d) at least one inverse thermosensitive polymer selected from poloxamer 124, poloxamer 188, poloxamer 237, poloxamer 338, poloxamer 407 and mixtures thereof;
    wherein said at least one inverse thermosensitive polymer is present in an amount below the critical gelation concentration (CGC), and wherein said composition remains in liquid phase up to a temperature of about 40° C. in vitro.

2. The pharmaceutical composition according to claim 1, wherein said composition has a viscosity below about 150 cP (centipoises).

3. The pharmaceutical composition according to claim 1, wherein said at least one inverse thermosensitive polymer is present in an amount below about 15% by weight, with respect to the weight of the composition.

4. The pharmaceutical composition according to claim 3, wherein said at least one inverse thermosensitive polymer is present in an amount between about 2% and about 14.5% by weight, with respect to the weight of the composition.

5. The pharmaceutical composition according to claim 4 wherein said at least one inverse thermosensitive polymer is present in an amount between about 5% and about 11% by weight, with respect to the weight of the composition.

6. The pharmaceutical composition according to claim 1, wherein said at least one poloxamer is poloxamer 188, poloxamer 407 or mixtures thereof.

7. The pharmaceutical composition according to claim 1, wherein said oily phase comprises at least one lipophilic compound.

8. The pharmaceutical composition according to claim 7, wherein said at least one lipophilic compound is a medium-chain triglycerides, soybean oil, sesame oil or almond oil.

9. The pharmaceutical composition according to claim 1, wherein said at least one surfactant is at least one non-ionic surfactant.

10. The pharmaceutical composition according to claim 9, wherein said at least one non-ionic surfactant is polysorbate 80 or polyoxyl-15-hydroxystearate.

11. The pharmaceutical composition according to claim 1, wherein said at least one surfactant is at least one ionic surfactant.

12. The pharmaceutical composition according to claim 11, wherein said at least one ionic surfactant is egg lecithin, hydrogenated phosphatidyl choline from egg lecithin, soybean lecithin or hydrogenated soybean lecithin.

13. The pharmaceutical composition according to claim 1, further comprising at least one co-surfactant wherein said at least one co-surfactant is propylene glycol, glycerol or sodium oleate.

14. The pharmaceutical composition according to claim 1, further comprising at least one dye wherein said at least one dye is a vital dye, a non-vital dye or a reactive dye.

15. The pharmaceutical composition according to claim 14, wherein said at least one dye is Lugol's solution, methylene blue, toluidine blue, crystal violet, indigo carmine, Congo red or phenol red.

16. The pharmaceutical composition according to claim 15, wherein said at least one dye is methylene blue.

17. A pharmaceutical composition in the form of an emulsion or a microemulsion comprising:
    (a) an aqueous phase;
    (b) an oily phase comprising medium-chain triglycerides;
    (c) a surfactant comprising polyoxyl-15-hydroxystearate;
    (d) an inverse thermosensitive polymer comprising poloxamer 188; and
    (e) methylene blue;
    wherein said poloxamer 188 is present in an amount below the critical gelation concentration (CGC), and wherein said composition remains in liquid phase up to a temperature of about 40° C. in vitro.

18. The pharmaceutical composition according to claim 17, which further comprises sodium chloride.

19. The pharmaceutical composition according to claim 17, wherein the composition comprises in w/v about 0.02% to about 1.0% of medium-chain triglycerides, about 0.08% to about 4% polyoxyl-15-hydroxystearate, about 5% to about 11% poloxamer 188, about 0.0005% to about 0.01% methylene blue and the remainder being water.

20. The pharmaceutical composition according to claim 18, wherein the composition comprises in w/v about 0.02% to about 1.0% of medium-chain triglycerides, about 0.08% to about 4% polyoxyl-15-hydroxystearate, about 5% to about 11% poloxamer 188, about 0.0005% to about 0.01% methylene blue, about 0.44% to about 0.5% sodium chloride and the remainder being water.

* * * * *